US006566500B1

(12) United States Patent
Vitetta et al.

(10) Patent No.: US 6,566,500 B1
(45) Date of Patent: May 20, 2003

(54) COMPOSITIONS AND METHODS FOR MODIFYING TOXIC EFFECTS OF PROTEINACEOUS COMPOUNDS

(75) Inventors: Ellen S. Vitetta, Dallas, TX (US); Victor F. Ghetie, Dallas, TX (US); Joan Smallshaw, Dallas, TX (US); Roxana G. Baluna, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/538,873

(22) Filed: Mar. 30, 2000

Related U.S. Application Data

(60) Provisional application No. 60/126,826, filed on Mar. 30, 1999.

(51) Int. Cl.[7] .......................... C07K 13/00; A61K 38/00
(52) U.S. Cl. .................... 530/350; 530/300; 530/391.7; 530/370; 530/396; 530/403; 514/2; 514/12; 435/69.1; 435/252.3; 435/320.1; 424/183.1; 536/23.1
(58) Field of Search ................................ 530/350, 370, 530/396, 391.7, 403; 424/183.1; 536/23.1; 435/69.1, 252.3, 320.1; 514/2, 12

(56) References Cited

U.S. PATENT DOCUMENTS

| | | | |
|---|---|---|---|
| 4,435,386 A | 3/1984 | Ribi et al. | 424/177 |
| 4,436,727 A | 3/1984 | Ribi | 424/177 |
| 4,436,728 A | 3/1984 | Ribi | 424/177 |
| 4,366,241 A | 10/1988 | Tom et al. | 435/7 |
| 4,866,034 A | 9/1989 | Ribi | 514/2 |
| 4,950,645 A | 8/1990 | Vosika et al. | 514/8 |
| 4,950,740 A | 8/1990 | Greenfield et al. | 530/350 |

FOREIGN PATENT DOCUMENTS

| | | | |
|---|---|---|---|
| WO | WO 91/16347 | 10/1991 | ............ C07K/9/00 |
| WO | WO 93/15113 | 8/1993 | ........... C07K/13/00 |
| WO | WO 94/13316 | 6/1994 | ......... A61K/37/352 |
| WO | WO 98/18820 | 5/1998 | ......... C07K/14/415 |
| WO | WO 99/60128 | 11/1999 | ........... C12N/15/26 |

OTHER PUBLICATIONS

Berndt et al., Mutagenic Analysis of a Receptor Contact Site on Interleukin–2: Preparation of an IL–2 Analog with Increased Potency. Biochemistry 33, 6571–6577 (1994).*
Obara et al., Site–Directed Mutagenesis of the Cell–Binding Domain of Human Fibronectin: Separable, Synergistic Sites mediate Adhesive Function. Cell 53, 649–657 (1988).*
Frankel et al. Role of Arginine 180 and Glutamic Acid 177 of Ricin Toxin A Chain in Enzymatic Inactivation of Ribosome. Mol. Cell. Biol. Vol. 10, 6257–6263 (1990).*
Frankel et al. Selection and Characterization of Ricin Toxin A–Chain Mutations in *Saccharomyces cerevisias*. Mol. Cell. Biol. vol. 9, 415–420 (1989).*

Hung et al. Cloning and Expression of Three Abrin A–chains and Their Mutants Derived by Site–Specific Mutagenesis in *Escherichia coli*. Eur. J. Biochem. 219 83–87 (1994).*
Baluna et al., "Evidence for a structure motif in toxins and interleukin–2 that may be responsible for binding to endothelial cells and initiating vascular leak syndrome," *PNAS USA*, 96(7):3957–3962, 1999.
Baluna et al., "The effect of a monoclonal antibody coupled to ricin A chain–derived peptides on endothelial cells in vitro: insights into toxin–mediated vascular damage," *Exper. Cell Res.*, 258(2):417–424, 2000.
Day et al., "Structure and activity of an active site substitution of ricin A chain," *Biochem.*, 35(34):11098–11103, 1996.
Jackson et al., "Mutational analysis of the Shiga toxin and Shiga–like toxin II enzymatic subunits," *J. Bacteriology*, 172(6):3346–3350, 1990.
Jackson et al., "Potent $\alpha_4\beta_1$ peptide antagonists as potential anti–inflammatory agents," *J. Med. Chem.*, 40(21):3359–3368, 1997.
Jia et al., "Function and disintegrin–like/cysteine–rich domains of atrolysin A: inhibition of platelet aggregation by recombinant protein and peptide antagonists," *J. Biol. Chem.*, 272(20):13094–13102, 1997.
Kagawa et al., "Crystal structure of the zymogen form of the group A Streptococcus virulence factor SpeB: an integrin–binding cysteine protease," *PNAS USA*, 97(5):258(2):2235–2240, 2000.
Stockbauer et al., "A natural variant of the cysteine protease virulence factor of group A Streptococcus with an arginine–glycine–aspartic acid (RGD) motif preferentially binds human integrins $\alpha_v\beta_3$ and $\alpha_{IIb}\beta_3$," *PNAS USA*, 96(1):242–247, 1999.
Vitetta et al., "Immunotoxins: magic bullets or misguided missiles?," *Immunology Today*, 14(6):252–259, 1993.
Baluna and Vitetta, "An in vivo model to study immunotoxin–induced vascular leak in human tissue," *J. Immunother.*, 22:41–47, 1999.
Baluna and Vitetta, "Vascular leak syndrome: A side effect of immunotherapy," *Immunopharmacology*, 37:117–132, 1996.

(List continued on next page.)

Primary Examiner—Karen Cochrane Carlson
Assistant Examiner—Chih-Min Kam
(74) Attorney, Agent, or Firm—Fulbright & Jaworski

(57) ABSTRACT

The present invention provides methods to produce immunotoxins (ITs) and cytokines with a reduced ability to promote vascular leak syndrome (VLS). The invention also provides ITs and cytokines which have been mutated to lack amino acid sequences which induce VLS. Also disclosed are methods for producing peptides that inhibit the induction of VLS by ITs and cytokines. Also disclosed are peptides comprising the (x)D(y) sequence to promote the extravasation of other molecules. Toxins mutated in the (x)D(y) motif or active site residues are disclosed for used in vaccines.

19 Claims, 10 Drawing Sheets

OTHER PUBLICATIONS

Baluna et al., "Fibronectin inhibits the cytotoxic effect of ricin A chain on endothelial cells," *Int. J. Immunopharm.,* 18:355–361, 1996.

Coulson et al., "Rotavirus contains integrin sequences and a disintegrin–like domain that are implicated in virus entry into cells," *Proc. Natl. Acad. Sci. U.S.A,* 94:5389–5394, 1997.

Downie et al., "Interleukin–2 directly increases albumin permeability of bovine and human vascular endothelium in vitro," *Am. J. Respir. Cell Molec. Biol.,* 7:58–65, 1992.

Dutcher et al., "A phase II study of high–dose continuous infusion interleukin–2 with lymphokine–activated killer cells in patients with metastatic melanoma," *J. Clin. Oncol.,* 9:641–648, 1991.

Engert et al., "The emerging role of ricin A–chain immunotoxins in leukemia and lymphoma," In: *Clinical Applications of Immunotoxins,* Frankel (ed.), 2:13–33, 1997.

Ghetie et al., "The GLP large scale preparation of immunotoxins containing deglycosylated ricin A chain and a hindered disulfide bond," *J. Immunol Methods,* 142:223–230, 1991.

Halling et al., "Genomic cloning and characterization of a ricin gene from *Ricinus communis,*" *Nucleic Acids Res.* 13:8019–8033, 1985.

Lamb et al., "Nucleotide sequence of cloned cDNA coding for preproricin," *Eur J Biochem,* 148:265–270, 1985.

M1sna et al., "Structure of recombinant ricin A chain at 2.3 Å," *Protein Sci.,* 2:429–435, 1993.

Munishkin and Wool, "Systematic deletion analysis of ricin A–chain function," *J. Biol. Chem.,* 270:30581–30587, 1995.

O'Hare et al., "Expression of ricin A chain in *Escherichia coli,*" *Febs Lett.,* 216:73–78, 1987.

Orucevic and Lala, "$N^G$–nitro–1–arginine methyl ester, an inhibitor of nitric oxide synthesis, ameliorates interleukin–2–induced capillary leak syndrome in healthy mice," *J. Immunother.,* 18:210–220, 1995.

Sausville and Vitetta, "Clinical studies with deglycosylated ricin a–chain immunotoxins," In: *Monoclonal Antibody–Based Therapy of Cancer,* Grossbard (ed.), 4:81–89, 1997.

Soler–Rodriguez et al., "Ricin A–chain and ricin A–chain immunotoxins rapidly damage human endothelial cells: implications for vascular leak syndrome," *Exp. Cell Res.,* 206:227–234, 1993.

Soler–Rodriguez et al., "The toxicity of chemically deglycosylated ricin a–chain in mice," *Int. J. Immunopharm.,* 14:281–291, 1992.

Takada et al., "Molecular and structural requirements of a lipoteichoic acid from *Enterococcus hirae* ATCC 9790 for cytokine–inducing, antitumor, and antigenic activities," *Infect. Immun.* 63:57–65, 1995.

Tselepis et al., An RGD to LDV motif conversion within the disintegrin kistrin generates an integrin antagonist that retains potency but exhibits altered receptor specificity, *J. Biol. Chem.,* 272:21341–21348, 1997.

Vial and Descotes, "Clinical toxicity of interleukin–2," *Drug Safety,* 7:417–433, 1992.

\* cited by examiner

FIG. 4

SEQUENCE LISTING

```
<160> NUMBER OF SEQ ID NOS: 19

<210> SEQ ID NO 1
<211> LENGTH: 267
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Met Val Pro Lys Gln Tyr Pro Ile Ile Asn Phe Thr Thr Ala Gly Ala
  1               5                  10                  15

Thr Val Gln Ser Tyr Thr Asn Phe Ile Arg Ala Val Arg Gly Arg Leu
             20                  25                  30

Thr Thr Gly Ala Asp Val Arg His Glu Ile Pro Val Leu Pro Asn Arg
         35                  40                  45

Val Gly Leu Pro Ile Asn Gln Arg Phe Ile Leu Val Glu Leu Ser Asn
     50                  55                  60
```

-continued

```
His Ala Glu Leu Ser Val Thr Leu Ala Leu Asp Val Thr Asn Ala Tyr
 65                  70                  75                  80

Val Val Gly Tyr Arg Ala Gly Asn Ser Ala Tyr Phe Phe His Pro Asp
                 85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205

Asn Ser Trp Gly Arg Leu Ser Thr Ala Ile Gln Glu Ser Asn Gln Gly
    210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
                245                 250                 255

Tyr Arg Cys Ala Pro Pro Pro Ser Ser Gln Phe
            260                 265

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Ala Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 251
<212> TYPE: PRT
<213> ORGANISM: Abrus precatorius
```

```
<400> SEQUENCE: 3

Glu Asp Arg Pro Ile Lys Phe Ser Thr Glu Ala Thr Ser Gln Ser
 1               5                  10                  15

Tyr Lys Gln Phe Ile Glu Ala Leu Arg Glu Arg Leu Arg Gly Gly Leu
                20                  25                  30

Ile His Asp Ile Pro Val Leu Pro Asp Pro Thr Thr Leu Gln Glu Arg
            35                  40                  45

Asn Arg Tyr Ile Thr Val Glu Leu Ser Asn Ser Asp Thr Glu Ser Ile
 50                  55                  60

Glu Val Gly Ile Asp Val Thr Asn Ala Tyr Val Val Ala Tyr Arg Ala
 65                  70                  75                  80

Gly Thr Gln Ser Tyr Phe Leu Arg Asp Ala Pro Ser Ser Ala Ser Asp
                85                  90                  95

Tyr Leu Phe Thr Gly Thr Asp Gln His Ser Leu Pro Phe Tyr Gly Thr
            100                 105                 110

Tyr Gly Asp Leu Glu Arg Trp Ala His Gln Ser Arg Gln Gln Ile Pro
        115                 120                 125

Leu Gly Leu Gln Ala Leu Thr His Gly Ile Ser Phe Phe Arg Ser Gly
130                 135                 140

Gly Asn Asp Asn Glu Glu Lys Ala Arg Thr Leu Ile Val Ile Ile Gln
145                 150                 155                 160

Met Val Ala Ala Ala Arg Phe Arg Tyr Ile Ser Asn Arg Val Arg
                165                 170                 175

Val Ser Ile Gln Thr Gly Thr Ala Phe Gln Pro Asp Ala Ala Met Ile
                180                 185                 190

Ser Leu Glu Asn Asn Trp Asp Asn Leu Ser Arg Gly Val Gln Glu Ser
            195                 200                 205

Val Gln Asp Thr Phe Pro Asn Gln Val Thr Leu Thr Asn Ile Arg Asn
        210                 215                 220

Glu Pro Val Ile Val Asp Ser Leu Ser His Pro Thr Val Ala Val Leu
225                 230                 235                 240

Ala Leu Met Leu Phe Val Cys Asn Pro Pro Asn
                245                 250

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Cys Gly Gly Gly Ser Val Thr Leu Ala Leu Asp Val Thr Asn Ala Tyr
 1               5                  10                  15

Val Gly Gly Gly
            20

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 5

Cys Gly Gly Gly Ser Val Thr Leu Ala Thr Asn Ala Tyr Val Gly Gly
 1               5                  10                  15
Gly

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Cys Gly Gly Gly Ser Val Thr Leu Ala Gly Gln Thr Thr Asn Ala Tyr
 1               5                  10                  15
Val Gly Gly Gly
             20

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Cys Gly Gly Gly Glu His Leu Leu Leu Asp Leu Gln Met Gly Gly Gly
 1               5                  10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Cys Gly Gly Gly Glu His Leu Leu Gln Met Gly Gly Gly
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu Ala Leu Asp Val Thr Asn Ala Tyr Val Val
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Leu Ala Ala Asp Val Thr Asn Ala Tyr Val Val
 1               5                  10
```

```
<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Leu Ala Leu Ala Val Thr Asn Ala Tyr Val Val
  1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Leu Ala Leu Glu Val Thr Asn Ala Tyr Val Val
  1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Leu Ala Leu Asn Val Thr Asn Ala Tyr Val Val
  1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Leu Ala Leu Asp Ala Thr Asn Ala Tyr Val Val
  1               5                  10

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gttacattag ccctggctgt caccaatgca tatg                              34

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 16
ctgttacatt agccctggaa gtcaccaatg catatg                                    36

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
ctttctgtta cattagccgc ggatgtcacc aatgcatatg                                40

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18
ctgttacatt agccctgaac gtcaccaatg catatgtgg                                 39

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
gttacattag ccctggatgc taccaatgca tatgtggtc                                 39
```

COMPOSITIONS AND METHODS FOR MODIFYING TOXIC EFFECTS OF PROTEINACEOUS COMPOUNDS

This application claims the priority of U.S. Provisional Application Ser. No. 60/126,826, filed Mar. 30, 1999, the disclosure of which is specifically incorporated herein by reference in its entirety.

BACKGROUND OF THE INVENTION

1. Field of the Invention

The present invention relates generally to the field of vascular leak, and particularly concerns toxins which induce or cause vascular leak syndrome (VLS). The invention provides immunotoxins (ITs) and cytokines which have been mutated to lack amino acid sequences which induce VLS and other toxic side effects. Disclosed are methods for mutating DNA segments encoding cytokines or immunotoxins so that an immunotoxin is produced that lacks sequences that induce VLS and other toxic side effects. Also disclosed are methods of preparing and using peptides which promote VLS and thus aid delivery of molecules into tissues. The present invention also relates to methods of preparing peptides which inhibit VLS and the used of mutated toxins as vaccines to protect immunized individuals from later toxicity.

2. Description of Related Art

VLS is often observed during bacterial sepsis and may involve IL-2 and a variety of other cytokines (Baluna and Vitetta, 1996). The mechanisms underlying VLS are unclear and are likely to involve a cascade of events which are initiated in endothelial cells (ECs) and involve inflammatory cascades and cytokines (Engert et al., 1997). VLS has a complex etiology involving damage to vascular endothelial cells (ECs) and extravasation of fluids and proteins resulting in interstitial edema, weight gain and, in its most severe form, kidney damage, aphasia, and pulmonary edema (Sausville and Vitetta, 1997; Baluna and Vitetta, 1996; Engert et al., 1997). Vascular leak syndrome (VLS) has been a major problem with all ITs thus far tested in humans, as well as cytokines such as interleukin 2 (IL-2), TNF and adenovirus vectors (Rosenberg et al., 1987; Rosensten et al., 1986).

ITs are hybrid molecules consisting of monoclonal antibodies (MAbs) or other cell-binding ligands, which are biochemically or genetically linked to toxins, toxin subunits, or ribosome inactivating proteins (RIPs) from plants, fungi or bacteria (Vitetta et al., 1993). Over the past two decades, ITs containing deglycosylated (dg) ricin A chain (dgRTA) have been developed, structurally optimized for stability and activity and evaluated for activity both in vitro, and in vivo in rodents, monkeys and humans (Vitetta et al., 1993; Sausville and Vitetta, 1997; Baluna and Vitetta, 1996).

It has been postulated that dgRTA-ITs induces VLS by damaging vascular endothelial cells (Soler-Rodriguez et al., 1993; Baluna et al., 1996). IL-2 and ITs prepared with the catalytic A chain of the plant toxin, ricin (RTA) and other toxins, damage human ECs in vitro and in vivo (Dutcher et al., 1991; Rosenberg et al., 1987; Vial and Descotes, 1992). Studies using human umbilical vein ECs (HUVECs) demonstrated that dgRTA or ITs prepared with dgRTA can damage these cells within one hour (Soler-Rodriguez et al., 1993) while the inhibition of protein synthesis required 4 hrs or longer. DgRTA-ITs also interfere with fibronectin (Fn)-mediated adhesion (Baluna et al., 1996). Fn inhibits dgRTA-mediated damage to human umbilical vein endothelial cells (HUVECS) (Baluna et al., 1996). Cell adhesion to Fn is mediated by integrins which recognize RGD and LDV sequences in the Fn molecule (Makarem and Humphries, 1991; Wayner and Kovach, 1992).

Three MAbs linked to dgRTA have been evaluated in Phase I trials in over 200 patients with relapsed chemorefractory lymphoma, myeloma, Hodgins disease and graft vs. host disease (GVHD) (Sausville and Vitetta, 1997). These ITs have shown no evidence of myelotoxicity or hepatotoxicity, but all have induced VLS at the maximum tolerated dose (MTD) as defined by hypoalbuminemia, weight gain, and in the most severe cases, pulmonary edema and hypotension (Baluna et al., 1996). In addition, they have induced myalgia and, in 3% of patients, rhabdomyalyosis at the MTD (Sausville and Vitetta, 1997); this side effect may also be related to VLS and result from muscle edema. Further, aphesias have occurred in <5% of patients' these may be due to edema in the cerebral microvasculture.

In certain aspects, the invention provides the use of a modified proteinaceous composition that has altered, relative to the sequence of a native proteinaceous composition, at least one amino acid of a sequence comprising (x)D(y), for the manufacture of a medicament for the treatment of a disease, including but not limited to GVHD, non-Hodgkin's and Hodgkin's lumphoma, myeloma, as well as metastatic lesions of solid tumors and damage to endothelial cells (i.e., VLS).

Clearly, further development of dgRTA-ITs as well as other ITs containing toxins and RIPS, as well as cytokines as clinical agents would be greatly facilitated by the elimination or reduction of VLS. If VLS could be avoided or reduced it would permit the use of much higher doses of a variety of therapeutic agents such as Its, gene therapy and cytokines without the dose limiting side effects currently encountered.

SUMMARY OF THE INVENTION

The present invention overcomes the deficiencies in the art by providing methods for modulating the ability of various proteinacious compounds to induce toxic effects, and proteinacious compounds that have been modified such that they have modulated ability to induce toxic effects. In some embodiments, the invention allows for the production of ITs with a reduced ability to promote or induce such toxic effects, including, for example, VLS. ITs made in accordance with the invention are for any number of therapeutic applications, for example, the treatment of GVHD, non-Hodgkin's and Hodgkin's lymphoma, myloma, and metastatic lesions tumors, in some particular aspects solid tumors. The present invention also provides methods for reducing the VLS promoting ability of proteinaceous compositions through a mutation of sequences that induce or promote any of a number of toxic effects. The present invention provides ITs, IL-2 TNF and adenovirus with a reduced ability to promote toxic effects, and methods of using such compounds.

The invention, in one aspect, provides a method of modifying the ability of a proteinaceous composition to induce a toxic effect, comprising the steps of: identifying at least one amino acid sequence comprising the sequence (x)D(y), wherein (x) is selected from the group leucine, isoleucine, glycine and valine, and wherein (y) is selected from the group valine, leucine and serine; and altering the amino acid sequence comprising the sequence (x)D(y). In certain embodiments, the altering comprises at least one mutation of the amino acid sequence. In other embodiments, the amino acid sequence is removed. In particular aspects, the amino acid sequence comprises the sequence (x)D(y), wherein the (x)D(y) sequence is GDL, GDS, GDV, IDL, IDS, IDV, LDL, LDS, LDV, LDS, VDL or VDV. In certain more specific embodiments, the invention provides a modified proteinaceous composition that has altered, relative to the sequence of a native proteinaceous composition, at least one amino acid of a sequence comprising (x)D(y), wherein (x) is selected from the group leucine, isoleucine, glycine and valine, and wherein (y) is selected from the group valine, leucine and serine, for use as a medicament.

In certain aspects, the composition has a reduced ability to induce at least one toxic effect. In other aspects, the altering enhances the ability of the composition to induce at least one toxic effect. In particular embodiments, the toxic effect is, for example, VLS, the ability to induce apoptosis, a disintigrin-like activity, the ability to damage EC cells or a combination thereof. Of course; those of ordinary skill will, by following the teachings of this specification, be able to determine additional toxic effect that may be modulated according to the methods disclosed herein. In some embodiments of the invention, it is desirable to decrease the level of the toxic effect. For example, there is great benefit to be gained by creating an IT which exhibits no, or lessened, VLS. In alternative embodiments, it will be desirable to increase the level of a given toxic effect. For example, if a proteinacious compound is being used to induce apoptosis in a therapeutic manner, then modifying the compound to increase the level of apoptosis could be beneficial. Those of ordinary skill in the art will be able to determine any of a number of manners in which to employ the modulation of toxic effects that can be had with the methods of the invention.

In some embodiments, the (x)D(y) sequence comprises a residue on the surface of the composition. In certain aspects, the altering occurs at one or more (x)D(y) tri-amino acid sequences. In certain embodiments, the (x)D(y) sequence comprises at least one flanking sequence. In particular aspects, the altering the sequence comprises at least one alteration within the at least one flanking sequence. In certain aspects, the at least one flanking sequence is mutated. In some facets, the at least one flanking sequence is removed. In other facets, the alteration occurs within of from about 1 to about 6 residues of an (x) or an (y) of a (x)D(y) tripeptide sequence. In some aspects, the flanking sequence is C-terminal to the (x)D(y) sequence. In other aspects, the flanking sequence is N-terminal to the (x)D(y) sequence. In a particular facet, the at least one flanking sequence comprises two flanking sequences, wherein the two flanking sequences are N-terminal and C-terminal to the (x)D(y) sequence.

The proteinacious composition can be any presently known of discovered in the future that has the (x)D(y) tripeptide sequence. In some embodiments, the proteinaceous composition comprises a toxin, a cytokine, a viral sequence or a combination thereof. In particular aspects, the toxin comprises a plant toxin, a fungal toxin, a bacterial toxin, a RIP or a combination thereof. In certain facets, the toxin comprises Abrin A chain, Diphtheria Toxin (DT) A-Chain, Pseudomonas exotoxin, RTA, Shiga Toxin A chain, Gelonin, Momordin, Pokeweed Antiviral Protein, Saporin, Trichosanthin, Barley toxin or a combination thereof In other embodiments, the proteinaceous composition comprises a cytokine, such as, for example, Interleukin-2. In further embodiments, the proteinaceous composition comprises a viral sequence, such as, for example, an adenoviral sequence. In certain aspects, the proteinaceous composition further comprises, or is comprised in, an IT.

The invention, in some particularly preferred aspects, the invention provides a method of reducing the ability of a proteinaceous composition to promote VLS, comprising the steps of: identifying at least one amino acid sequence comprising the sequence (x)D(y), as defined above.

In certain aspects other aspects, the invention provides the use of a modified proteinaceous composition that has altered, relative to the sequence of a native proteinaceous composition, at least one amino acid of a sequence comprising (x)D(y), for the manufacture of a medicament for the treatment of a disease, including but not limited to GVHD, non-Hodgkin's and Hodgkin's lymphoma, myloma, as well as metastatic lesions of solid tumors and damage to endothelial cells (i.e., VLS).

The invention additionally provides a method of preparing an IT with a reduced ability to induce a toxic effect, comprising the steps of: identifying at least one amino acid sequence comprising the sequence (x)D(y); removing the amino acid sequence from the toxin; and conjugating the toxin to a composition comprising at least one antibody to produce an IT, wherein the IT produced possesses a reduced ability to promote a toxic effect when compared to a like IT wherein the amino acid sequence was not removed from the toxin.

The invention also provides a method of enhancing the ability of a proteinaceous composition to induce extravasation, comprising adding at least one amino acid sequence comprising (x)D(y) to the composition. In particular aspects, the composition comprises a peptide. In further aspects, the extravasation of the composition or at least one molecule is enhanced. In some embodiments, the composition is covalently conjugated to the at least one molecule. In certain facets, the extravasation of the molecule is enhanced. In additional facets, the molecule is a therapeutic agent, such as, for example, at least one IT, antibody, cytokine, virus or a combination thereof.

The invention further provides a method of reducing the toxic effects of a proteinaceous material in a patient, comprising administering to a patient a composition that mimics a sequence comprising (x)D(y). In particular aspects, the proteinaceous material comprises at least one (x)D(y) sequence. In additional aspects, the composition comprises at least one amino acid sequence comprising the sequence (x)D(y), wherein the amino acid sequence has been altered to possess an reduced ability to promote a toxic effect. In certain facets, the composition comprises at least one peptide.

The invention also provides a modified proteinaceous composition that has altered, relative to the sequence of a native proteinaceous composition, at least one amino acid of a sequence comprising (x)D(y), prepared according to the methods described above and elsewhere in this specification. In certain embodiments, the proteinaceous composition comprises a toxin, a cytokine, a viral sequence or a combination thereof. In certain aspects, the toxin is, for example, a plant toxin, a fungal toxin, a bacterial toxin, a RIP or a combination thereof. In additional aspects, the toxin comprises Abrin A chain, Diphtheria Toxin (DT) A-Chain, Pseudomonas exotoxin, RTA, Shiga Toxin A chain, Gelonin, Momordin, Pokeweed Antiviral Protein, Saporin, Trichosanthin, Barley toxin or a combination thereof. In other embodiments, the proteinaceous composition comprises a cytokine, such as for example, Interleukin-2. In other aspects, the proteinaceous composition comprises a viral sequence, such as, for example, an adenoviral sequence.

In certain facets, the composition further comprises an antibody. In particular aspects, the composition further comprises an IT. In additional facets, the IT further comprises at least a second agent, such as, for example, at least one effector molecule. In particular aspects, the effector molecule is a toxin, an anti-tumor agent, a therapeutic enzyme, an antiviral agent, a virus, a cytokine, a growth factor, or a combination thereof. In other facets, the agent is at least one reporter molecule.

The invention additionally provides an IT, comprising at least one proteinaceous molecule with a reduced ability to induce VLS, apoptosis, disintegrin-like activity or EC damage, wherein the proteinaceous molecule has at least one (x)D(y) or flanking sequence altered.

The invention provides a modified proteinaceous composition with an enhanced ability to promote extravasation, wherein the composition comprises at least one amino acid sequence comprising a (x)D(y) tripeptide or a flanking sequence relative to the native sequence.

In certain embodiments, the composition comprises a therapeutic agent, such as, for example, at least one IT, antibody, cytokine, virus or a combination thereof. In specific embodiments, the composition and the therapeutic agent are covalently conjugated. In particular facets, the composition is a therapeutic agent.

The invention also provides a RTA with a reduced ability to promote toxicity in a patient, wherein the (x)D(y) sequence comprising positions 74 to 76 is altered. In certain embodiments, the leucine at position 74 is altered, the aspartate at position 75 is altered, and/or the valine at position 76 is altered. In specific facets, the (x)D(y) sequence further comprises positions of from about 1 to about 6 residues of an (x) or an (y) of the (x)D(y) tripeptide sequence.

The invention also provides a method of reducing the ability of a proteinaceous composition to induce VLS, comprising the steps of: identifying at least one amino acid sequence (x)D(y); and altering, removing or mutating the amino acid sequence.

Flanking regions to the (x)D(y) tri-peptide sequence may be altered to reduce a proteinaceous composition's ability to induce VLS. As used herein, a "proteinaceous composition" refers to a protein of greater than about 200 amino acids or the full length endogenous sequence translated from a gene, a polypeptide of greater than about 100 amino acids, and/or a peptide of from about 3 to about 100 amino acids, including peptides of 3, 4, 5, 6, etc., 10, 11, 12, 13, 14, etc., 20, 21, 22, etc, 30, 40, 50, 60, etc. 100, 110, 120, etc. 200, 220, 240, etc, 300, 350, 400, etc, 500, 600, 700, etc., and 1000 amino acids in length. In an aspect the C-terminal flanking amino acid sequence may be altered, mutated or removed if it is a threonine (T). In certain aspects, this method of altering this sequence and/or flanking amino acids is by removal of the amino acid sequence.

The invention provides a proteinaceous composition that has a reduced ability to induce VLS. In an aspect aspect, the proteinaceous composition that has been altered to remove at least one amino acid sequence contiguous with the composition comprising the sequence (x)D(y). In certain aspects of the present invention, the proteinaceous composition may be a ribosome-inactivating protein (RIP), including but not limited to gelonin, momordin, pokeweed antiviral protein (PAP), saporin, or trichosanthin; a toxin or toxin subunit, including but not limited to abrin A chain, diphtheria toxin (DT) A-chain, Pseudomonas exotoxin-A (PE38-lys), RTA, Shiga toxin A chain, or barley toxin; a cytokine including but not limited to IL-2. Proteins, polypeptides and/or peptides may be derived from RIPs, toxins or cytokines to be used in the methods and compositions of the present invention. In certain aspects, the proteinaceous composition may be used to make an IT with a reduced ability to promote or enhance VLS. In other aspects, the proteinaceous composition for use in an IT is a RIP and/or toxin sequence.

In other aspects of the present invention, proteins, peptides and/or polypeptides may be made that include the VLS-inducing sequence. These VLS-inducing proteinaceous compositions may be used to promote VLS, and increase the extravasation of molecules into tissues. In additional aspects of the present invention, proteinaceous compositions may be made that lack the VLS-inducing sequence. Such compositions may be used as inhibitors of agents that induce VLS in vivo or adenoviral vectors for gene therapy. The compositions of the present invention may be made by synthetic peptide synthesis or through the use of recombinant genetic technology, as would be known to those of ordinary skill in the art in light of the present disclosure. Toxin mutants lacking VLS activity can also be effective for protecting individuals against the native toxin.

As used herein the specification, "a" or "an" may mean one or more. As used herein in the claim(s), when used in conjunction with the word "comprising", the words "a" or "an" may mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) SCID mice with vascularized human skin xenografts were injected with 200 μg of RFB4-dgRTA (solid), RFB4-LDV$^+$ (open), RFB4-GQT (cross-hatched) or saline (hatched), and the wet/dry weight ratios of biopsies of the human skin were determined. (FIG. 1B) SCID mice were injected as described in FIG. 1A and the wet/dry weight ratios of lungs were determined. The values represent the mean of three experiments±SD. The asterisks indicate a statistically significant difference from saline (−) treated mice (*,p<0.02, **p<0.01).

(FIG. 2A) $10^5$ HUVECs were incubated on ice for 30 min with FITC-dgRTA, in the presence or absence of 100-fold excess of dgRTA (solid), RFB4-LDV$^+$ (crosshatched), RFB4 (shaded), Fn (hatched) or PE38-lys (open) in 100 ul PBS/BSA/Azide. The percent inhibition of binding to HUVECs is presented. The values represent the means±SD of three studies. (FIG. 2B) The same as FIG. 2A, except the $10^5$ HUVECs were incubated on ice for 30 min with FITC-RFB4-LDV$^+$.

Figure 4:
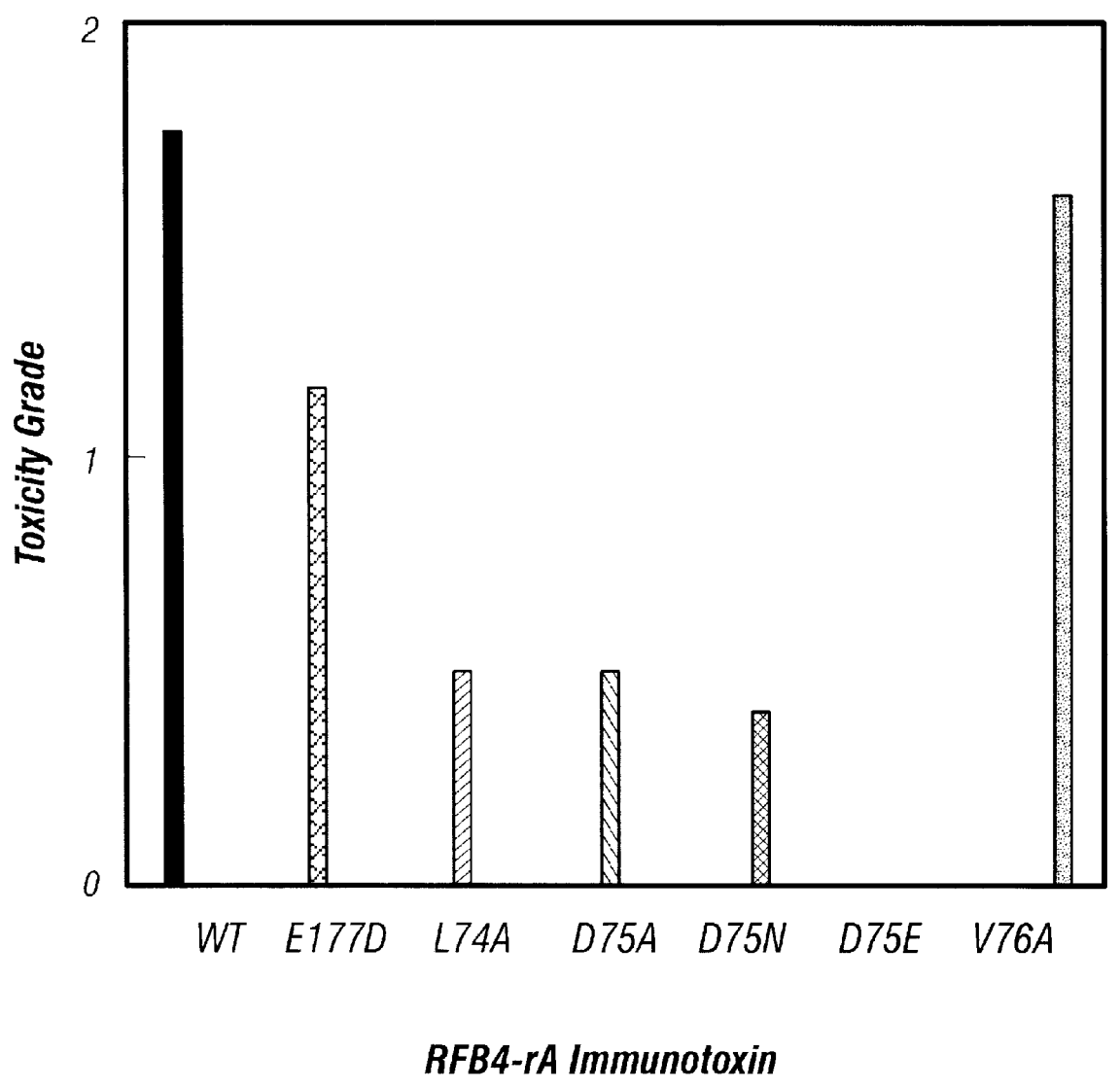

FIG. 4. Effect of RFB4-rRTA ITs on the morphology of HUBEC monolayers. HUVEC monolayers were incubated at 37° C. for 18 h with 100 µg/ml of RFB4rRTA ITs in M199 medium with 2% fetal calf serum. Morphological changes were scored as: –, no changes; rounding up of cells; and ++ disruption and detachment of cells from the monolayer. The toxicity grade was represented as a ratio (number of "+"/ number of experiments).

(FIG. 5A) The body weights were determined. (FIG. 5B) The wt/dry wt ratio of lungs were determined.

DESCRIPTION OF ILLUSTRATIVE EMBODIMENTS

Figure 1A:
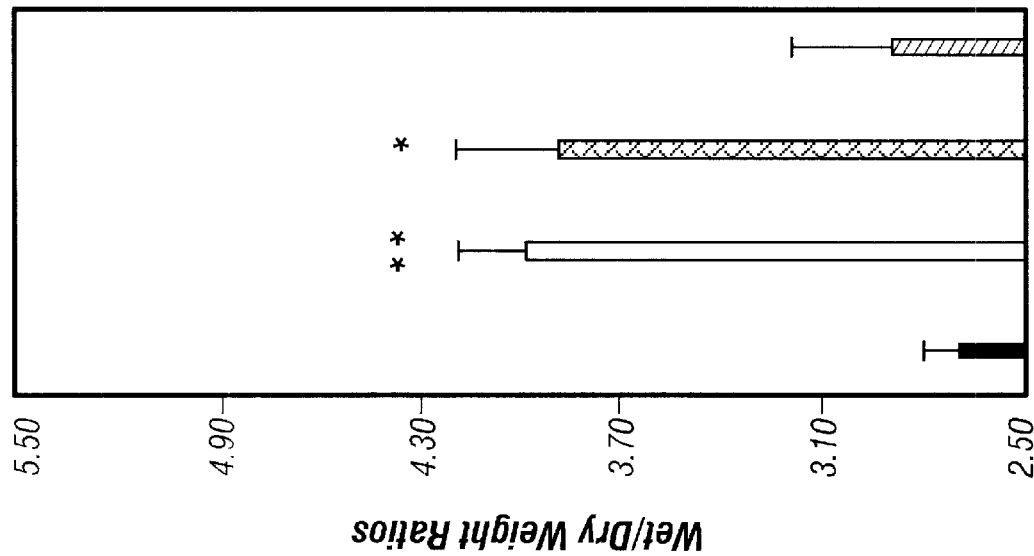
FIGS. 1A and 1B. The in vivo effect of RFB4-RTA-peptides.

Cell damage, particularly endothelial cell damage, whether produced by toxins, such as from snake bites or molecules causing septic shock, or therapeutic agents, such as ITs or interleukins, remains a problem for patients. Types of cell damage include VLS, disinitigrin-like activities and apoptosis.

To devise methods and compositions to alleviate VLS, candidate sequences of molecules which cause VLS were evaluated to determine whether RTA, toxins, RIPS and IL-2 might share structural motifs responsible for interfering with cell-cell and cell-matrix interactions, and thereby damage human ECs. In comparing the sequences of VLS-inducing toxins, RIPS and IL-2, a (x)D(y) consensus motif was identified where (x) could be L, I, G or V and (y) could be V, L or S. In the case of RTA and IL-2, molecular modeling indicated that these motifs were completely or substantially exposed on the surface of their respective molecules. A similar motif is shared by viral disintegrins, which disrupts the function of integrins, indicating that RTA, IL-2 and perhaps other toxins may damage ECs by virtue of their (x)D(y) motifs and hence, may be disintegrins.

This vascular-leak promoting activity of this motif was surprising and unexpected, since LDV homologue sequences also play a role in the vascular functions of a variety of non-toxic molecules including vascular cell adhesion molecule 1 (VCAM-1), which contains the IDS sequence, and the γ chain of fibrinogen, which contains the GDV sequence (Clements et al., 1994). LDV constitutes the minimal active site in the CS 1 domain of fibronectin responsible for its binding to the $\alpha_4\beta_1$ integrin receptor (Makarem and Humphries, 1991; Wayner and Kovach, 1992; Nowlin et al., 1993). Though fibronectin possesses this sequence, it does not damage HUVECs. Instead, FN protects HUVECs from RTA-mediated damage (Baluna et al., 1996), in direct contrast to the VLS activity of toxic agents that possess this motif.

To determine whether this motif was responsible for EC damage, short LDV or LDL containing peptides from RTA or IL-2, respectively, were generated, attached to a mouse MAb and studied their ability to bind to and damage HUVECs in vitro and to damage mouse lung vasculature and human vasculature in skin xenografts in vivo. One active site mutant of RTA and several LDV mutants were generated. These LDV mutants contained conservative changes which, when modeled, would not be expected to affect the active site of the RTA. Antibody-conjugated peptides from RTA containing the sequence (L74, D75, V76), but not peptides with deleted or altered sequence, induced EC damage in vitro and vascular damage in vivo in the two animal models (Baluna et al., 1999). These results demonstrated that the VLS-inducing site does not require the active site. It is contemplated that the noncontiguous active site of the RTA, which does not encompass LDV, is either not required to damage ECs, or only partly contributes to vascular damage.

These results demonstrate that an active site may not be required to induce vascular damage, and that one or more active peptides or polypeptides may be made with reduced VLS promoting activity. With this discovery, it is now possible that one or more amino acid deletion(s) or mutation (s) of the (x)D(y) sequence(s), and/or at least one region flanking the sequence, may reduce or prevent VLS and improve the therapeutic index or the tolerated dose of VLS-inducing molecules. It is expected that one or more peptides and small molecule drug inhibitors comprising at least one mutated motif and/or one or more flanking sequence can be created that reduce or eliminate the VLS induced by VLS promoting agents.

In certain embodiments, it is contemplated that disintegrin or disintegrin-like activity of proteinaceous compositions may be reduced or enhanced. Disintegrins possess various activitie(s) including an ability to damage ECs, an ability to interfere with cell adherence and/or an ability to interfere with platelet aggregation. It is contemplated that one or more amino acid deletion(s) or mutation(s) of the (x)D(y) sequence(s), and/or one or more flanking residues, may reduce or prevent the disintegrin-like activity of one or more molecules comprising these sequences. It is expected that one or more peptides and small molecule drugs inhibitors comprising at least one mutated motif and/or one or more flanking sequence can be created that reduce or eliminate the disintegrin-like activity of such agents.

Additionally, the LDV site of RTA induced apoptosis in ECs. It has been reported that many toxins and ITs induce apoptosis as well as inhibit protein synthesis. It is also contemplated that one or more amino acid deletion(s) or mutation(s) of the (x)D(y) sequence(s), and/or at least one flanking region, may reduce or prevent the apoptotic activity of one or more molecules comprising these sequences. It is expected that one or more peptides and small molecule drug inhibitors comprising at least one mutated motif and/or at least one flanking sequence can be created that reduce or eliminate the apoptotic activity of such agents. Thus apoptotic activity may cause or contribute to toxin or cytokine induced VLS.

It is also contemplated that one or more amino acid deletion(s) or mutation(s) of the (x)D(y) sequence(s), and/or one or more flanking residues, may reduce or prevent the ability of molecules comprising these sequences to induce EC damage. It is expected that one or more peptides and small molecule drug inhibitors comprising at least one mutated motif and/or one ore more flanking residuces can be created that reduce or eliminate the EC damaging activity of such agents.

Described herein below are methods and compositions with reduced or enhanced VLS promoting abilities based upon mutations in the (x)D(y) or (x)D(y)T sequences within proteins, polypeptides, peptides or other proteinaceous materials which remove or add such sequences, respectively. It is contemplated that the same mutations described for reducing or enhancing VLS promoting ability will also reduce or enhance, respectively, the apoptotic activity, EC damaging and/or one or more disintegrin-like activities of polypeptides, peptides or proteins. Thus, it will be understood that all methods described herein for producing proteins, polypeptides and peptides with enhanced or reduced VLS promoting ability will be applied to produce proteins, polypeptides and peptides with reduced apoptotic activity, EC damaging and/or one or more disintegrin-like activities. All such methods, and compositions identified or produced by such methods, are encompassed by the present invention.

A. Identification of an (X)D(Y) Motif in VLS-Inducing Agents

Homologous structural motifs in RTA, other toxins, RIPs and IL-2, which may affect cell-cell and cell-matrix interactions and thereby damage human ECs, have been identified and tested for their ability to promote VLS in model systems. The (x)D(y) motif where x=L, I, G or V and y=V, L or S (Table 1) is common in the sequences of RTA, other toxins, RIPs and cytokines which induce VLS. This motif is also shared by viral disintegrins which disrupt the function of integrins (Coulson et al., 1997).

1. Localization of (x)D(y) motifs in RTA, Disintegrins, PE38-lys and IL-2

With the discovery of the importance of the (x)D(y) sequence in promoting VLS, it is now possible to create RTA mutants which will retain their enzymatic activity, which is important for making effective ITs, but which also have their VLS-inducing properties reduced.

The LDV motif in RTA (residues 74–76, SEQ ID NO:1) is at the C-terminus of a β-strand of the first domain near the Tyr-80 residue which is involved in the active site (Mlsna etal., 1993). The active site (residues 80, 123, 177, 180,211) of the enzyme does not include the LDV sequence so that the enzymatic activity of RTA should not be affected by mutations or deletions in this sequence (Munishkin and Wool, 1995).

To examine the crystal structure of RTA and IL-2, space filling models of the three dimensional structures of RTA (PDB accession number 1br5.pdb) and IL-2 (PDB accession number 1irl.pdb) were compared with the atoms of the LDV residues of RTA, the LDL residues of IL-2, and the active site residues of RTA (Y80, Y123, E177, R180, N209 and W211). The models were generated with the Insight II program (MSI). Examinations of the crystal structure of RTA indicate that this motif is only partially exposed, but structural fluctuations in the molecule may increase its accessibility. From this and other data described herein, it is contemplated that either alterations in the (x)D(y) motif, the C-terminal flanking amino acid(s), the N-terminal flanking amino acid(s), or a combination thereof, may result in the loss of VLS-inducing activity by a variety of agents.

TABLE 1

Non-Limiting Examples of (x)D(y) Motifs in Molecules Which Induce VLS

| Category | Agent inducing VLS | (X)D(Y) Motif | Location | GenBank or GenPept Accession # |
|---|---|---|---|---|
| Toxins[1] | Abrin A chain | IDV | 68–70 | X76721 |
| | | GDL | 114–116 | |
| | | VDS | 229–231 | |
| | Barley toxin | LDV | 171–173 | U77463 |
| | Diphtheria Toxin (DT) A-Chain | VDS | 6–8 | 576189 |
| | | VDS | 28–30 | |
| | | IDS | 289–291 | |
| | | LDV | 441–443 | |
| | Pseudomonas exotoxin-(PE38-lys)[2] | GDL | 348–350 | K01397 |
| | | GDV | 430–432 | |
| | | GDL | 605–607 | |
| | Ricin Toxin A-Chain (RTA) | LDV | 74–76 | A23903 |
| | Shiga toxin A chain | VDS | 36–38 | M19437 |
| | | IDS | 63–65 | |
| | | VDV | 74–76 | |
| | | GDS | 132–134 | |
| | | LDL | 162–164 | |
| | | VDL | 219–221 | |
| RIPs[3] | Gelonin | IDV | 114–116 | L12243 |
| | Momordin | LDV | 64–66 | 576194 |
| | | LDS | 132–134 | |
| | Momordin | LDS | 165–167 | P16094 |
| | Pokeweed Antiviral Protein (PAP) | VDS | 179–181 | X98079 |
| | | GDL | 308–310 | |
| | Saporin | LDL | 6–8 | X69132 |
| | | IDL | 143–145 | |
| | Trichosanthin | GDV | 23–25 | U25675 |
| | | IDV | 87–89 | |
| | | LDS | 155–157 | |
| Cytokines | Interleukin-2 (IL-2) | LDL | 19–21 | 1311005 |

[1]The enzymatically active chain of the holotoxin
[2]PE38 refers to enzymatically active Domain III (residues 405 to 613) plus residues 253–354 and 381–404 in PE.
[3]Ribosome-inactivating proteins (RIPs) which are homologues of the enzymatically active A chains of plant toxins Another family of proteins called disintegrins usually contain an RGD sequence. In the case of one disintegrin, which is present in rotavirus, an LDV sequence is present (Coulson et al., 1997). Disintegrins damage ECs or interfere with cell adherence and/or platelet aggregation (McLane et al., 1998; Huang, 1998; Tselepis et al., 1997). In the snake venom disintegrin kistrin, LDV can be substituted for RGD without compromising disintegrin function (Tselepis et al., 1997). Thus, RTA and a variety of other molecules may be disintegrins which share properties with kirstin (Blobel and White, 1992; Lazarus and McDowell, 1993) in damaging human ECs. In certain embodiments, it is contemplated that disintegrins or molecules that possess disintegrin-like activity may be altered or produced to possess a reduced ability to damage ECs, a reduced ability to interfere with cell adherence and/or a reduced ability to interfere with platelet aggregation. Such molecules may be produced by mutating at least one residue in the peptide mimics of the (x)D(y) and/or flanking sequences may be made that block the activity of disintegrins.

In PE38-lys the GDL sequence is distal from the active site (Li et al., 1995). Thus, it is contemplated that PE38-lys may be similarly mutated to reduce or eliminate its VLS promoting activity without completely eliminating its activity.

In IL-2, the LDL sequence at residues 19–21 (SEQ ID NO:2) is located in an α-helix and is also partially exposed. A mutation in Asp-20, in the LDL motif (Table 1) eliminates binding of IL-2 to the β chain of the IL-2 receptor and subsequent cell proliferation (Collins et al., 1988). It has been reported that IL-2 directly increases the permeability of the vascular endothelium to albumin in vitro and that this effect can be inhibited by anti-IL-2 receptor MAbs (Downie et al., 1992). The results of Example 1 demonstrate that the LDL sequence in IL-2 damages HUVECs. However, in contrast to RTA, the Asp-20 in the LDL of IL-2 is involved in receptor binding and functional activity (Collins et al., 1988). Thus, it is contemplated that in certain embodiments, mutations in IL-2's (x)D(y) sequence and/or flanking sequence(s) to eliminate or reduce VLS must preserve the Asp-20 or the biological activity of IL-2 may be reduced.

2. Mutations in Flanking Sequences

The (x)D(y) sequence may not be solely responsible for the promotion of VLS. In certain embodiments, it is contemplated that additional sequences that flank the (x)D(y) sequence may be mutated to enhance or reduce a peptide, polypeptide or protein's ability to promote VLS.

For example, LDV constitutes the minimal active site in the CS1 domain of fibronectin responsible for its binding to the $α_4β_1$ integrin receptor (Makarem and Humphries, 1991; Wayner and Kovach, 1992; Nowlin et al., 1993). However, fibronectin (FN) does not damage HUVECs. Instead, FN protects HUVECs from RTA-mediated damage (Baluna et al., 1996). Unlike RTA, FN has a C-terminal LDV-flanking proline instead of a threonine.

In disintegrins, residues flanking RGD, play a role in ligand binding (Lu et al., 1996). The difference between the ability of an LDV or homologue-containing molecule to promote vascular integrity (e.g., FN) or disrupt it (e.g., RTA) may depend on the orientation, or availability for interaction (i.e., binding), of the LDV motif and hence, on flanking sequences. Therefore, a change in one or more amino acids of this sequence or one or more amino acids of the N- or C-terminal flanking sequences may convert a molecule from one that damages endothelial cells (distintegrin-like) to one that enhances their growth. It is contemplated that changes in one or more flanking residues of the (x)D(y) sequence may enhance or reduce the ability of a molecule to promote VLS. It is further contemplated that changes that expose the (x)D(y) sequence to the external surface of the protein so as to interact with other proteins, such as receptors, would enhance VLS promoting activity, while conformations that are less exposed may reduce VLS promoting activity.

B. Production of Compositions with Altered VLS Activity

With the identification of the (x)D(y) and the (x)D(y)T motifs as inducing VLS, inducing apoptosis, and other effects, it is possible that the creation of a new family of molecules of VLS inhibitors will allow these molecules to exert maximal beneficial effects. For example, a reduced toxicity of anti-cancer therapeutic agents using the compositions and methods disclosed herein may allow larger tumors or more advanced disease to be treated. It is now possible to identify or synthesize small drug molecule(s) which block the interaction between cells and VLS promoting, apoptosis promoting, EC damaging, and/or distintegrin-like molecules. In certain embodiments, peptides or drug-mimetics based on the (x)D(y) and/or (x)D(y)T motif or its flanking sequences may be used to inhibit VLS or other activities in vivo. It is possible to create peptides or peptide-carrier conjugates which compete with the LDV motif binding site on endothelial cells and prevent VLS or other actions in a variety of other situations including sepsis, IL-2 therapy, etc.

In certain embodiments, it is also possible that one or more (x)D(y), (x)D(y)T motifs and/or particular flanking sequences added to larger molecules will increase extravasation into tissues. In light of the present disclosure, peptides containing (x)D(y) and/or (x)D(y)T sequences being tested as anti-inflammatory or anti-metastatic agents (Jackson et al., 1997; Maeda et al., 1997; Greenspoon et al., 1994) should be monitored for both increased extravasation and for toxic effects on vasculature. However, in certain embodiments, it may be desirable to produce proteinaceous compositions that enhance extravasation into tissues. Improvement in extravasation of a therapeutic composition, or promoting extravasation for a therapeutic composition with a protein, polypeptide or peptide of the present invention may allow greater access of the therapeutic agent to tissues. Thus, methods of enhancing or decreasing extravasation of one or more proteins, polypeptides, peptides or therapeutic agents are provided. Preferred therapeutic agents include, but are not limited to one or more ITs, antibodies, cytokines, virus, drugs and the like.

To produce peptides, polypeptides or proteins that lack the (x)D(y) and/or (x)D(y)T sequence, one could delete or mutate the conserved aspartic acid (D), substitute another amino acid for the aspartic acid, or insert one or more amino acids at or adjacent to its position. Any amino acid that may replace the (D) residue in the sequence as a consequence of a deletion or mutation event.

Alternatively the (x) residue could be deleted, substituted, or moved by the insertion of one or more amino acids, to remove the (x)D(y) and/or (x)D(y)T sequence. Any amino acid that may replace the (x) residue in the sequence as a consequence of the deletion or mutation event is preferably not leucine (L), isoleucine (I), glycine (G) or valine (V).

Or the (y) residue could be deleted, substituted, or moved by the insertion of one or more amino acids, to remove the (x)D(y) and/or (x)D(y)T sequence. Any amino acid that may replace the (y) residue in the sequence as a consequence of the deletion or mutation event is preferably not valine (V), leucine (L) or serine (S).

Additionally, the (x)D(y) and/or (x)D(y)T sequences can be removed by any mutation that alters or changes this sequence. Such mutations include but are not limited to truncations, insertions, substitutions and deletions of amino acids. It is contemplated that chemical modification may also alter a (x)D(y) and/or (x)D(y)T sequence to reduce its ability to induce or promote VLS.

Thus, it is contemplated that such mutations that affects the (x)D(y) sequence or flanking sequence may alter the ability of a polypeptide to promote VLS or other abilities associated with these sequences. For example, one preferred agent that produced VLS is abrin A chain (GenBank Accession number X76721; SEQ ID NO:3), which contains an IDV sequence at positions 68–70 of its amino acid sequence. A glycine (G) is at position 67. Therefore, a deletion of the isoleucine at position 68 would result in the glycine at position 67 to be directly adjacent to the aspartic acid residue (D) at original position 69. The new sequence created would then be GDV at positions 67–69 of the mutated abrin A chain. This new tripeptide sequence still matches the VLS-inducing sequence (x)D(y) and/or (x)D(y)T. However, it is contemplated that since such a deletion would shift the position of the tri-amino acid sequence in the structure of the mutated abrin A chain protein, polypeptide or peptide being produced. A shift in the position of the tri-amino acid sequence may move it into a less favorable position to contact any cell, receptor or molecule to promote or induce VLS. The resulting mutated abrin A chain protein, polypeptide or peptide may have a reduced ability to promote or induce VLS, and thus would be encompassed by the present invention.

Similarly, other toxins or compounds that induce VLS, including but not limited to those listed in Table 1, can be mutated so that one or more (x)D(y) and/or one or more flanking residues are removed (i.e., mutated). However, it is contemplated that to produce toxins or compounds that have a reduced ability to induce VLS, it is preferable that any remaining (x)D(y) and/or (x)D(y)T sequences to have a reduced exposure to the surface of the protein, polypeptide or peptide.

For example, it is contemplated that (x)D(y) and/or (x)D(y)T sequences that are at least partly located in the non-exposed portions of a protein, polypeptide or peptide, or otherwise masked from full or partial exposure to the surface of the molecule, would interact less with cells, receptors or other molecules to promote or induce VLS. Thus, it is contemplated that the complete elimination of (x)D(y) and/or (x)D(y)T sequences from the primary structure of the protein, polypeptide or peptide is not necessary to produce toxins or molecules with a reduced ability to induce or promote VLS. However, removal of all (x)D(y) and/or (x)D(y)T sequences is preferred to insure the composition has the least ability to induce or promote VLS.

To determine whether a mutation would likely produce a protein, polypeptide or peptide with a less exposed (x)D(y) and/or (x)D(y)T motif, the putative location of the moved or added (x)D(y) and/or (x)D(y)T sequence could be determined by comparison of the mutated sequence to that of the unmutated protein, polypeptide or peptide's secondary and tertiary structure, as determined by such methods known to those of ordinary skill in the art including, but not limited to, X-ray crystallography, NMR or computer modeling. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis. The Entrez database is crosslinked to a database of 3-D structures for the identified amino acid sequence, if known. Such molecular models may be used to identify (x)D(y), (x)D(y)T and/or flanking sequences in peptides and polypeptides that are more exposed to contact with external molecules, (e.g. receptors) than similar sequences embedded in the interior of the polypeptide or polypeptide. It is contemplated that (x)D(y), (x)D(y)T and/or flanking sequences that are more exposed to contact with external molecules are more likely to contribute to promoting or reducing VLS and other toxic effects associated with these sequences, and and thus should be primary targets for mutagenesis. In certain embodiments, when adding at least one (x)D(y), (x)D(y)T and/or flanking sequence is desirable, regions of the protein that are more exposed to contact with external molecules are preferred as sites to add such a sequence. The mutated or wild-type protein, polypeptide or peptide's structure could be determined by X-ray crystallography or NMR directly before use in in vitro or in vivo assays, as would be known to one of ordinary skill in the art.

Once an amino acid sequence comprising a (x)D(y) and/or (x)D(y)T sequence is altered in a peptide, polypeptide or protein, or added to a peptide, polypeptide or protein, changes in its ability to promote at least one toxic effect may be assayed by any of the techniques described herein or as would be known to one of ordinary skill in the art.

As used herein, "alter", "altered", "altering", "alteration" of an amino acid sequence comprising a (x)D(y) sequence or a (x)D(y)T sequence may include chemical modification of an amino acid sequence comprising a (x)D(y) and/or a (x)D(y)T sequence in a protein, polypeptide or peptide as would be known to those of ordinary skill in the art, as well as any mutation of such an amino acid sequence including but not limited to insertions, deletions, truncations, or substitutions. It is preferred that such changes alters at least one toxic effect (i.e., the ability to promote VLS, EC damage, apoptosis, disintigrin-like activity) of one or more amino acid sequence(s) comprising a (x)D(y) and/or (x)D(y)T sequences. As used herein an amino acid sequence comprising a (x)D(y) sequence or a (x)D(y)T sequence may comprise at least one flanking sequence C- and/or N-terminal to a (x)D(y) and/or a (x)D(y)T tri- or quatra-peptide sequence. Such an "alteration" may be made in synthesized peptides, or in nucleic acid sequences that are expressed to produce mutated proteins, polypeptides or peptides.

In an aspect of the invention, the alteration of an amino acid sequence comprising a (x)D(y) and/or a (x)D(y)T sequence comprises removal of the amino acid sequence. As used herein "remove", "removed", "removing" or "removal" of an amino acid sequence comprising a (x)D(y) and/or a (x)D(y)T sequence refers to a mutation in the primary amino acid sequence that eliminates the presence of the (x)D(y) and/or a (x)D(y)T tri- or quatra-peptide sequence, and/or at least one native flanking sequence. The terms "removed" or "lacks" may be used interchangably.

For example, it is contemplated that mutations including but not limited to at least one insertion or substitution of at least one amino acid selected from the group phenylalanine (F); cysteine/cystine (C); methionine (M); alanine (A); threonine (T); serine (S); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position (x) of one or more (x)D(y) and/or (x)D(y)T sequences would reduce its ability to promote VLS. Table 2 below lists exemplary, but not limiting, modified or unusual amino acids that are contemplated as useful in certain aspects of the invention.

TABLE 2

Modified and Unusual Amino Acids

| Abbr. | Amino Acid |
| --- | --- |
| Aad | 2-Aminoadipic acid |
| BAad | 3-Aminoadipic acid |
| BAla | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | Allo-Hydroxylysine |
| 3Hyp | 3-Hydroxyproline |
| 4Hyp | 4-Hydroxyproline |
| Ide | Isodesmosine |
| Aile | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

It is also contemplated that mutations including but not limited to at least one insertion or substitution of at least one amino acid selected from the group isoleucine (I); valine (V); leucine (L); phenylalanine (F); cysteine/cystine (C); methionine (M); alanine (A); glycine (G); threonine (T); serine (S); tryptophan (W); tyrosine (Y); proline (P); histidine (H); glutamic acid (E); glutamine (Q); asparagine (N); lysine (K); and arginine (R), and including, but not limited to, those shown at Table 2 at the position (D) of one ore more (x)D(y) and/or (x)D(y)T sequences would reduce its ability to promote VLS.

It is contemplated that mutations including but not limited to at least one insertion or substitution of at least one amino acid selected from the group isoleucine (I); phenylalanine (F); cysteine/cystine (C); methionine (M); alanine (A); glycine (G); threonine (T); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position (y) of one or more (x)D(y) and/or (x)D(y)T sequences would reduce its ability to promote VLS.

Amino acids that flank either the (x) or (y) residue of the (x)D(y) sequence may also contribute to its ability to promote VLS. For example, is it contemplated that mutations including but not limited to at least one insertion or substitution of at least one amino acid selected from the group isoleucine (I); valine (V); leucine (L); phenylalanine (F); cysteine/cystine (C); methionine (M); alanine (A); glycine (G); serine (S); tryptophan (W); tyrosine (Y); proline (P); histidine (H); glutamic acid (E); glutamine (Q); aspartic acid (D); asparagine (N); lysine (K); and arginine (R), and including, but not limited to, those shown at Table 2 at the position T of one or more (x)D(y)T sequences would reduce its ability to promote VLS.

It is further contemplated that at least one mutation, chemical modification, movement or other alteration in the N- or C-terminal flanking sequences of the (x)D(y) and/or (x)D(y)T sequence would also produce proteins, polypeptides or peptides that have a reduced ability to promote VLS. Preferably, such mutations or alterations would occur in one or more residues which will not effect the active site. In other embodiments, the mutations or alterations would occur in one or more residues of from about 1, about 2, about 3, about 4, about 5, about 6 or more N-terminal and/or C-terminal to the (x)D(y) tripeptide sequence. In other aspects, one or more residues that are not adjacent to the (x)D(y) tripeptide may contribute to the function of the (x)D(y) motif. Such residues may be identified by their proximity to the tripeptide sequence in a 3-dimentional model, as described herein and as would be known to one of ordinary skill in the art, and are contemplated for alteration as part of a flanking sequence. Such alterations may include any of those described above for altering the (x)D(y) and (x)D(y)T sequences, as long as one or more "wild type" flanking residues are altered, removed, moved, chemically modified, etc.

Proteins, polypeptides and peptides produced using the methods of the present invention that have a reduced ability to induce VLS would have application in serving as protective agents against VLS produced by compositions containing the (x)D(y) and/or (x)D(y)T sequence. It is contemplated that such proteins, polypeptides and peptides may serve as inhibitors that block the activity of the (x)D(y) and/or (x)D(y)T sequence. Additionally, such proteins, polypeptides and peptides may be used in the creation of ITs with a reduced ability to produce VLS.

1. Mutagenesis

In certain aspects, mutagenesis of nucleic acids encoding peptides, polypeptides or proteins may be used to produce the desired mutations to enhance or reduce a composition's ability to promote VLS, apoptosis or other effects associated with the (x)D(y) and flanking sequences. Mutagenesis may be conducted by any means disclosed herein or known to one of ordinary skill in the art.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

As specific amino acids may be targeted, site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the mutation site being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement. Alternatively, a pair of primers may be annealed to two separate strands of a double stranded vector to simultaneously synthesize both corresponding complementary strands with the desired mutation(s) in a PCR™ reaction.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

2. Recombinant Vectors, Host Cells and Expression

The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein, polypeptide or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid coding for the gene product to control RNA polymerase initiation and expression of the gene.

The promoter may be in the form of the promoter that is naturally associated with a gene, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. Nos. 4,683,202 and 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a gene in its natural environment. Such promoters may include promoters normally associated with other genes, and/or promoters isolated from any other bacterial, viral, eukaryotic, or mammalian cell, and/or promoters made by the hand of man that are not "naturally occurring," i.e., containing difference elements from different promoters, or mutations that increase, decrease, or alter expression.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is contemplated that proteins, polypeptides or peptides may be co-expressed with other selected proteins, wherein the proteins may be co-expressed in the same cell or a gene(s) may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both the gene(s) and the other selected protein in the same recombinant cell.

As used herein, the terms "engineered" and "recombinant" cells or host cells are intended to refer to a cell into which an exogenous DNA segment or gene, such as a cDNA or gene encoding a protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant protein, polypeptide or peptide, whether mutant or wild-type, in accordance with the present invention one would prepare an expression vector that comprises a wild-type, or mutant protein-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 h, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

It is contemplated that the proteins, polypeptides or peptides produced by the methods of the invention may be "overexpressed", i.e., expressed in increased levels relative to its natural expression in cells. Such overexpression may be assessed by a variety of methods, including radiolabeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

3. Proteins, Polypeptides, and Peptides

The present invention also provides purified, and in preferred embodiments, substantially purified, proteins, polypeptides, or peptides. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally-obtainable state, i.e., relative to its purity within a cellular extract. A purified protein, polypeptide, or peptide therefore also refers to a wild-type or mutant protein, polypeptide, or peptide free from the environment in which it naturally occurs.

The nucleotide and protein, polypeptide and peptide sequences for various genes have been previously disclosed, and may be found at computerized databases known to those of ordinary skill in the art. One such database is the National Center for Biotechnology Information's Genbank and Gen-Pept databases. The coding regions for these known genes may be amplified and/or expressed using the techniques disclosed herein or by any technique that would be know to those of ordinary skill in the art. Additionally, peptide sequences may be sythesized by methods known to those of ordinary skill in the art, such as peptide synthesis using automated peptide synthesis machines, such as those available from Applied Biosystems (Foster City, Calif.).

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present invention, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present invention provides DNA sequences for the specific proteins, any fusion protein purification method can now be practiced. This is exemplified by the generation of an specific protein-glutathione S-transferase fusion protein, expression in $E.$ $coli$, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

4. Antibodies

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with an immunogenic protein composition or comprising a target epitope in accordance with the present invention and collecting antisera from that immunized animal.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g, a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp2/0-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729–6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in *E. coli*.

C. ITS

Toxins and/or Mabs may be derived from natural sources or produced using recombinant DNA technology. At least one toxin and at least one antibody may be combined to form an "ITn". ITs combine into a single molecule, the exquisite specificity of a ligand and the extraordinary toxicity of a toxin. Despite their conceptual simplicity, ITs are large and complex molecules that are continually undergoing improvements for optimal in vivo activity since each of their common components, e.g., one or more a binding moieties, one or more cross-linkers, and one or more toxins, introduces a different set of problems that must be addressed for the IT to function optimally in vivo.

Any antibody of sufficient selectivity, specificity or affinity may be employed as the basis for an IT. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

The origin or derivation of the antibody or antibody fragment for use in the invention (e.g., Fab', Fab or F(ab')$_2$) is not crucial to the practice of the invention, so long as the antibody or fragment that is employed has the desired properties for the ultimately intended use of the IT. Thus, where monoclonal antibodies are employed, they may be of human, murine, monkey, rat, hamster, chicken or even rabbit origin. The invention also contemplates the use of human antibodies, "humanized" or chimeric antibodies from mouse, rat, or other species, bearing human constant and/or variable region domains, single chain antibodies, Fv domains, as well as recombinant antibodies and fragments thereof. Of course, due to the ease of preparation and ready availability of reagents, murine Mabs will typically be preferred.

In certain therapeutic embodiments, one may use known antibodies, such as those having high selectivity for solid tumors, such as B72.3, PRBC5 or PR4D2 for colorectal tumors; HMFG-2, TAG 72, SM-3, or anti-p 185.sup.Her2 for breast tumors; anti-p 185.sup.Her2 for lung tumors; 9.2.27 for melanomas; MO v18 and OV-TL3 for ovarian tumors, and anti-Id, CD19, CD22, CD25, CD7 and CD5 for lymphomas and leukemias. Anti-CD2, anti-CD25, anti-CD4 and anti-CD45R° ITs may be purified according to the invention and used to kill malignant T cells or HIV-infected cells. Also, CD3-specific ITs as well as CD4 and CD25 specific ITs may be purified and used to prevent acute GVHD after bone marrow transplantation.

In other embodiments, one may use another immunogen and prepare a new Mab. The technique for preparing Mabs is quite straightforward, and may be readily carried out using techniques well known to those of skill in the art, as exemplified by the technique of Kohler & Milstein (1975). Generally, immunogens are injected intraperitoneally into mice. This process is repeated three times at two-weekly intervals, the final immunization being by the intravenous route. Three days later the spleen cells are harvested and fused with SP2/0 myeloma cells by standard protocols (Kohler & Milstein, 1975): Hybridomas producing antibodies with the appropriate reactivity are then cloned by limiting dilution.

The toxins that have been used to form ITs are derived from bacteria or plants and are inhibitors of protein synthesis. They are among the most powerful cell poisons known. Fewer than ten molecules will kill a cell if they enter the cytosol (although many times that number must bind to the cell surface because the entry process is inefficient). This extraordinary potency initially led to the concern that such poisons were too powerful to control. However, the toxins can be rendered innocuous (except when directed to the target cells) simply by removing or modifying their cell-binding domain or subunit. The remaining portion of the toxin (lacking a cell-binding domain) is then coupled to a ligand (e.g., an antibody) that targets the toxic portion to the target cell. By selecting an antibody lacking unwanted cross-reactivity, ITs are safer and have fewer non-specific cytotoxic effects than most conventional anticancer drugs. The other main attraction of toxins is that because they are inhibitors of protein synthesis, they kill resting cells as efficiently as dividing cells. Hence, tumor or infected cells that are not in cycle at the time of treatment do not escape the cytotoxic effect of an IT.

"Toxin" is employed herein to mean any anticellular agent, and includes but is not limited to cytotoxins and any combination of anticellular agents. In the case of chemotherapeutic agents, agents such as a hormone, a steroid for example; an antimetabolite such as cytosine arabinoside, fluorouracil, methotrexate or aminopterin; an anthracycline; mitomycin C; a vinca alkaloid; demecolcine; etoposide; mithramycin; or an antitumor alkylating agent such as chlorambucil or melphalan, may be used.

However, preferred toxins will be plant-, fingus- or bacteria-derived toxins, which, by way of example, include various A chain toxins, particularly RTA; RIPs such as saporin or gelonin, α-sarcin, aspergillin or restrictocin; ribonucleases such as placental ribonuclease; angiogenin, diphtheria toxin, and Pseudomonas exotoxin, to name just a few. The exemplary toxins that can be mutated to remove or alter the placement of sequences that induce VLS are listed in Table 1.

Plant holotoxin often contain two disulfide-bonded chains, the A and B chains. The B chain carries both a cell-binding region (whose receptor is often uncharacterized) and a translocation region, which facilitates the insertion of the A chain through the membrane of an acid intracellular compartment into the cytosol. The A chain then kills the cell after incorporation. For their use in vivo, the ligand and toxin must be coupled in such a way as to remain stable while passing through the bloodstream and the tissues and yet be labile within the target cell so that the toxic portion can be released into the cytosol.

The most preferred toxin moiety for use in connection with the invention is RTA, and particularly toxin A chain which has been treated to modify or remove carbohydrate residues, so-called dgRTA. Recombinant A chain expressed in *E. coli* and also lacking carbohydrates can be used. In certain embodiments, RTA may be made as described herein below in Example 3.

However, it may be desirable from a pharmacologic standpoint to employ the smallest molecule possible that nevertheless provides an appropriate biological response. One may thus desire to employ smaller A chain peptides or other toxins which will provide an adequate anti-cellular response. To this end, it has been discovered by others that RTA may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin moiety will provide additional significant benefits in accordance the invention. In that the cloning and expression of biologically active RTA and other VLS-inducing toxins have now been enabled through the publications of others (O'Hare et al., 1987; Lamb et al., 1985; Halling et al., 1985), it is now possible to identify and prepare smaller or otherwise variant peptides which nevertheless exhibit an appropriate toxin activity. Moreover, the fact that RTA and other VLS-inducing toxins have now been cloned allows the application of site-directed mutagenesis, through which one can readily prepare and screen for A chain and other VLS-inducing toxins, toxin-derived peptides and obtain additional useful moieties for use in connection with the present invention. Once identified, these moieties can be mutated to produce toxins with a reduced ability to promote VLS, apoptosis, disintegrin-like activity, EC damaging activity and other effects of such sequences described herein or known to one of skill in the art.

Fusion-ITs with PE, DT-A, etc. in any combination are made by recombinant DNA technology as would be known to one of ordinary skill in the art. Antibodies, cytokines or soluble receptor DNA may be used in such preparations.

The cross-linking of many, but not all toxins, of the conjugate with the binding agent region is an important aspect of the invention. In the case of RTA, if one desires a conjugate having biological activity, it is believed that a cross-linker which presents a disulfide function is required. The reason for this is unclear, but is likely due to a need for the toxin moiety to be readily releasable from the binding agent once the agent has "delivered" the toxin inside the targeted cells. Each type of cross-linker, as well as how the cross-linking is performed, will tend to vary the pharmacodynamics of the resultant conjugate. Ultimately, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Cross-linking reagents are used to form molecular bridges that tie together functional groups of two different proteins (e.g., a toxin and a binding agent). To link two different proteins in a step-wise manner, heterobifinctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the crosslinker, already tied up to the first protein, reacts with the cysteine residue (free sulfhydryl group) of the other protein (e.g., dgRTA).

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

The most preferred cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to crosslink functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane. The use of such cross-linkers is well understood in the art.

1. IT Conjugates

The present invention provides ITs against target epitopes, such as epitopes expressed on a diseased tissue or a disease causing cell. In certain embodiments the IT comprises at least one toxin described herein. In other embodiments the IT or toxin further comprises at least a second agent. Such an agent may be a molecule or moiety. Such a molecule or moiety may comprise, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, anti-viral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of at least a second agent comprises at least one detectable label. "Detectable labels" are compounds and/or elements that can be detected due to their specific functional properties, and/or chemical characteristics, the use of which allows the antibody to which they are attached to be detected, and/or further quantified if desired.

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

2. Methods for IT Preparation

Methods of making and preparing ITs are known to those of ordinary skill in the art. Such methods are disclosed in U.S. Pat. Nos. 5,686,072, 5,578,706, 4,792,447, 5,045,451, 4,664,911, and 5,767,072, each incorporated herein by reference). The toxin moiety of the IT may be any one of a variety of toxins that are commonly employed in the art. It may be an intact toxin, a toxin A chain, or a naturally occurring single-chain RIP. Toxins which are encompassed by the invention include, but are not limited to, diphtheria toxin (DT) and DT(CRM-45); pseudomonas endotoxin derived PE38; RTA and abrin and blocked forms of both of these; gelonin and saporin.

ITs comprising Mabs covalently bound to dgRTA by hindered disulfide linkers have recently entered clinical trials for the treatment of non-Hodgkin's (B cell) lymphoma, Hodgkin's lymphoma neplasms or GVHD. These "second generation" ITs are stable, long lived and display potent cytotoxicity to target cells. Standardized procedures for rapid preparation of high yields of these ITs have been developed (Ghetie et al., 1991).

The procedure for preparation of the ITs with, for example, dgRTA comprises the derivitization of Mabs with SMPT and reduction of dgRTA with dithiothreitol (DTT), followed by the reaction of the two components to establish a hindered interchain disulfide bond. The chemical crosslinking reaction results in a mixture of antibody, toxin and ITs which are then purified, initially to remove the free antibody and free toxin molecules and subsequently to separate the different IT species which comprise one antibody molecule conjugated with one, two, three or more than three toxin molecules, respectively. The unreacted components of the crosslinking reaction may be removed by successive chromatographies on an affinity chromatography column such as activated dye/agarose to remove free antibody followed by gel filtration to remove high molecular weight material and free toxin.

The result of this procedure is a mixture of conjugates of various toxin/antibody ratios. An important embodiment of the present invention is the further purification of this mixture to obtain preparations essentially comprising ITs of a single toxin/antibody ratio separated from ITs of different toxin/antibody ratios. This purification is accomplished by further chromatographic separation which may be accomplished by affinity chromatography for example, using a salt gradient to elute the various species of ITs and gel filtration to separate the ITs from larger molecules.

Another important embodiment of the present invention is the ability to determine which of the toxin/IgG ratios is the most effective cytotoxic agent to be used in pharmacological preparations. The isolation and characterization of each of the single species of IT made possible by the present invention is of particular advantage in clinical applications as it allows the practitioner to exercise more precise control over the effective amount of IT to be administered in a particular situation.

3. Gel Filtration

A gel to be used in the procedures of the present invention is a three dimensional network which has a random structure. Molecular sieve gels comprise cross-linked polymers that do not bind or react with the material being analyzed or separated. For gel filtration purposes, the gel material is generally uncharged. The space within the gel is filled with liquid and the liquid phase constitutes the majority of the gel volume. Materials commonly used in gel filtration columns include dextran, agarose and polyacrylamide.

Dextran is a polysaccharide composed of glucose residues and is commercially available under the name SEPHADEX (Phamacia Fine Chemicals, Inc.). The beads are prepared with various degrees of cross-linking in order to separate different sized molecules by providing various pore sizes. Alkyl dextran is cross-linked with N,N'-methylenebisacrylamide to form SEPHACRYL-S100 to S1000 which allows strong beads to be made that fractionate in larger ranges than SEPHADEX can achieve.

Polyacrylamide may also be used as a gel filtration medium. Polyacrylamide is a polymer of cross-linked acrylamide prepared with N,N'-methylenebisacrylamide as the cross-linking agent. Polyacrylamide is available in a variety of pore sizes from Bio-Rad Laboratories (USA) to be used for separation of different size particles.

The gel material swells in water and in a few organic solvents. Swelling is the process by which the pores become filled with liquid to be used as eluant. As the smaller molecules enter the pores, their progress through the gel is retarded relative to the larger molecules which do not enter the pores. This is the basis of the separation. The beads are available in various degrees of fineness to be used in different applications. The coarser the bead, the faster the flow and the poorer the resolution. Superfine is to be used for maximum resolution, but the flow is very slow. Fine is used for preparative work in large columns which require a faster flow rate. The coarser grades are for large preparations in which resolution is less important than time, or for separation of molecules with a large difference in molecular weights. For a discussion of gel chromatography, see Freifelder, Physical Biochemistry, Second Edition, pages 238–246, incorporated herein by reference.

The most preferred methods of gel filtration for use in the present invention are those using dextran gels, such as SEPHADEX, and those using dextran-polyacrylamide gels such as SEPHACRYL which are able to separate molecules in the 180 to 240 kilodalton range.

4. Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are that the matrix must adsorb molecules, the ligand must be coupled without altering its binding activity, a ligand must be chosen whose binding is sufficiently tight, and it must be possible to elute the substance without destroying it.

A preferred embodiment of the present invention is an affinity chromatography method wherein the matrix is a reactive dye-agarose matrix. Blue-SEPHAROSE, a column matrix composed of Cibacron Blue 3GA and agarose or SEPHAROSE may be used as the affinity chromatography matrix. The most preferred matrix is SEPHAROSE CL-6B available as Reactive Blue 2 from Sigma Chemical Company, catalogue #R 8752. This matrix binds the ITs of the present invention directly and allows their separation by elution with a salt gradient.

5. ELISA

ELISAs may be used in conjunction with the invention. In an ELISA assay, proteins or peptides incorporating toxin A chain sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN. These added agents also tend to assist in the reduction of nonspecific background. The layered antisera is then allowed to incubate for from 2 to 4 hours, at temperatures preferably on the order of 25° C. to 37° C. Following incubation, the antisera-contacted surface is washed so as to remove non-immunocomplexed material. A preferred washing procedure includes washing with a solution such as PBS/TWEEN, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

D. Vaccination

The present invention contemplates vaccines for use in immunization embodiments. It is contemplated that proteinaceous compositions that are less effective in promoting VLS or other toxic effects by alterations in one or more (x)D(y), (x)D(y)T and/or flanking sequences may be useful as antigens. In particular embodiments, peptides comprising one or more (x)D(y), (x)D(y)T and/or flanking sequences are contemplated as useful antigens. Preferably the antigenic material is extensively dialyzed to remove undesired small molecular weight molecules and/or lyophilized for more ready formulation into a desired vehicle. In other embodiments, it is also possible to use toxins lacking one or more active site residues (i.e., a toxoid) as vaccines.

1. Immunomodulators

It is contemplated that immunomodulators can be included in the vaccine to augment the patient's response. Immunomodulators can be included as purified proteins or their expression engineered into the cells when cells are part of the composition. The following sections list examples of immunomodulators that are of interest.

a. Cytokines

Interleukins and cytokines, and vectors expressing interleukins and cytokines are contemplated as possible vaccine components. Interleukins and cytokines, include but not limited to interleukin 1, IL-2, IL-3, IL-4, IL-5, IL-6, IL-7, IL-8, IL-9, IL-10, IL-11-, IL-12, IL-13, IL-14, IL-15, β-interferon, α-interferon, γ-interferon, angiostatin, thrombospondin, endostatin, METH-1, METH-2, GM-CSF, G-CSF, M-CSF, tumor necrosis factor, TGFβ, LT and combinations thereof.

b. Chemokines

Chemokines or genes that code for chemokines also may be used as vaccine components. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

The preparation of polyvalent vaccine is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously, intradermally or intramuscularly. Additional formulations which are suitable for other modes of administration include suppositories and, in some cases, oral or nasal formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The polyvalent vaccine of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations. The intramuscular route may be preferred in the case of toxins with short half lives in vivo.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Arecel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

2. Adjuvants

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

The present invention contemplates that a variety of adjuvants may be employed in the membranes of cells, such as tumor cells, resulting in an improved immunogenic composition. The only requirement is, generally, that the adjuvant be capable of incorporation into, physical association with, or conjugation to, the cell membrane of the cell in question.

Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram⁻ cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Hemocyanins and hemoerythrins may also be used in the invention. The use of hemocyanin from keyhole limpet (KLH) is particularly preferred, although other molluscan and arthropod hemocyanins and hemoerythrins may be employed.

Various polysaccharide adjuvants may also be used. For example, Yin et al., (1989) describe the use of various pneumococcal polysaccharide adjuvants on the antibody responses of mice. The doses that produce optimal responses, or that otherwise do not produce suppression, as indicated in Yin et al., (1989) should be employed. Polyamine varieties of polysaccharides are particularly preferred, such as chitin and chitosan, including deacetylated chitin.

A further preferred group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645 and PCT Patent Application WO 91/16347, which have not previously been suggested for use with cellular carriers, are now proposed for use in the present invention.

A preferred adjuvent in the present invention is BCG. BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Azuma et al., (1988) show that trehalose dimycolate administration correlates with augmented resistance to influenza virus infection in mice. Trehalose dimycolate may be prepared as described in U.S. Pat. No. 4,579,945.

BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Recently developed molecular genetic tools and methods for mycobacteria have provided the means to introduce foreign genes into BCG (Jacobs et al., 1987; Snapper et al., 1988; Husson et al., 1990; Martin et al., 1990). Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE®BCG (Organon Inc., West Orange, N.J.).

In a typical practice of the present invention, cells of Mycobacterium bovis-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are re-suspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of preferred adjuvants for use with the immunogens of the present invention. Nonionic block copolymer surfactants (Rabinovich et al., 1994; Hunter et al., 1991) may also be employed. Oligonucleotides, as described by Yamamoto et al., (1988) are another useful group of adjuvants. Quil A and lentinen complete the currently preferred list of adjuvants. Although each of the agents, and the endotoxins described below, are well-known as adjuvants, these compounds have not been previously incorporated into the membrane of a target cell, as shown herein.

One group of adjuvants particularly preferred for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants to prepare multi-adjuvant-incorporated cells. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

E. Pharmaceutical Preparations

Pharmaceutical aqueous compositions of the present invention comprise an effective amount of one or more IT, VLS inhibitory peptide or polypeptide, VLS stimulatory peptide or polypeptide and/or cytokine dissolved or dispersed in a pharmaceutically acceptable carrier or aqueous medium. The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The following buffers and reagents are particularly contemplated for use in the preparation of pharmaceutical preparations of the present invention: dgRTA, deglycosylated ricin A chain; DMF, dimethylformamide (Pierce, Rockford, Ill.); DTT (Pierce); PBE, 0.05M sodium phosphate, pH 7.5 with 1 mM EDTA; PBES, 0.05M sodium phosphate, pH 7.5 with various concentrations of NaCl (such as 0.1M, 0.2M, 0.3M, 0.4M and 0.5M NaCl) and 1 mM EDTA; PBSE, 0.01M sodium phosphate, pH 7.5 with 0.17M NaCl and 1 mM EDTA; SMPT, N-succinimidyl-oxycarbonyl-α-methyl-α(2-pyridyldithio)toluene (Pierce). All buffers may be prepared with endotoxin-free distilled water using enzyme grade salts (Fisher Biotec, Springfield, N.J.).

The ITs, peptides or polypeptides and/or cytokines may be formulated for parenteral administration, e.g., formulated for injection via the intravenous, intramuscular or subcutaneous routes, though other routes such aerosol administration may be used. The preparation of an aqueous composition that contains at least one IT, proteinaceous material and/or cytokine as an active ingredient will be known to those of skill in the art in light of the present disclosure, as exemplified by Remington's Pharmaceutical Sciences, 16th Ed. Mack Publishing Company, 1980, incorporated herein by reference. Moreover, for human administration, it will be understood that preparations should meet sterility, pyrogenicity, general safety and purity standards as required by FDA Office of Biological Standards.

Typically, such compositions can be prepared as injectables, either as liquid solutions or suspensions; solid forms suitable for preparing solutions or suspensions upon the addition of a liquid prior to injection can also be prepared; and the preparations can also be emulsified. The compositions will be sterile, be fluid to the extent that easy syringability exists, stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Although it is most preferred that solutions of ITs, peptide or polypeptides and/or cytokines be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

It is particularly contemplated that suitable pharmaceutical IT, peptide or polypeptide compositions will generally comprise, but are not limited to, from about 10 to about 100 mg of the desired IT conjugate, peptide or polypeptide admixed with an acceptable pharmaceutical diluent or excipient, such as a sterile aqueous solution, to give a final concentration of about 0.25 to about 2.5 mg/ml with respect to the conjugate, in, for example, 0.15M NaCl aqueous solution at pH 7.5 to 9.0. The preparations may be stored frozen at −10° C. to −70° C. for at least 1 year.

F. Kits

In still further embodiments, the present invention concerns kits for use with the IT or vaccination methods described above. Toxins, cytokines or antigenic compositions with reduced VLS promoting or toxic effects may be provided in a kit. Such kits may be used to combine the toxin with a specific antibody to produce an IT, provide cytokines with reduced toxicity, or provide antigens for vaccination in a ready to use and storable container. Additionally, peptide inhibitors of VLS producing sequences or proteinaceous enhancers of extravasation may be included in a kit. However, kits including combinations of such components may be provided. The kits will thus comprise, in suitable container means, a proteinaceous composition with reduced or enhanced VLS promoting activity. The kit may comprise an antibody or IT in suitable container means.

The container means of the kits will generally include at least one vial, test tube, flask, bottle, syringe and/or other container means, into which the at least one protein, polypeptide or peptide may be placed, and/or preferably, suitably aliquoted. The kits of the present invention may include a means for containing at least one antibody, IT and/or any other reagent containers in close confinement for commercial sale. Such containers may include injection and/or blow-molded plastic containers into which the desired vials are retained.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Structural Motif for Initiating Vascular Leak Syndrome

This example demonstrates that a three amino acid sequence motif, (x)D(y), in toxins and IL-2 is responsible for damaging vascular ECs. Short (<20 amino acid) (x)D(y) motif-containing peptides from RTA or IL-2 which contained flanking glycines and a cysteine, as well as peptides with deleted or mutated sequences were generated. These peptides were attached via the cysteine to a mouse IgG1 Mab (RFB4) not reactive with HUVECs. The VLS-inducing ability of this IgG-peptide conjugate (IgG-RTA) in three VLS model systems was compared. The first was in vitro damage to human umbilical endothelial cells, (HUVECs) (Soler-Rodriguez et al., 1993); the second was in vivo fluid accompanied in mouse lungs (Baluna and Vitetta, 1996); and the third was in vivo human skin xenografts in SCID mice (Baluna and Vitetta, 1998).

Peptide Synthesis. A peptide representing 13 amino acids (residues 69–81, SEQ ID NO:1) from RTA, with added N- and C-terminal glycine residues to improve solubility (Table 3), was synthesized. The peptides containing the x(D)y motif were difficult to solubilize even with the additional three flanking glycines on each end of the peptide. For this reason, they were conjugated to a soluble carrier protein. The MAb RFB4 was chosen because the RFB4-dgRTA is a prototypic IT, and therefore RFB4-peptides should "mimic" ITs.

An N-terminal cysteine was added to couple the peptide to the RFB4 MAb. Two RTA control peptides (Table 3) were synthesized. A peptide of 9 amino acids representing residues 15–23 from IL-2 as well as a control peptide (Table 3) was also synthesized. Again, flanking glycines and a cysteine were added. All peptides were synthesized on an Applied Biosystems Model 430A Solid-phase Peptide Synthesizer.

TABLE 3

Peptides from RTA and IL-2[1]

| Origin | Designation | Type | Peptide Sequence |
|---|---|---|---|
| RTA | LDV+<br>SEQ ID NO:4 | Native | CysGlyGlyGlySerValThrLeuAla<u>LeuAspVal</u>ThrAsnAlaTyrValGlyGlyGly<br>                        69 70  71 72  73 74  75  76 77 78  79  80 81 |
|  | LDV−<br>SEQ ID NO:5 | Deleted | CysGlyGlyGlySerValThrLeuAlaThrAspAlaTyrValGlyGlyGly<br>                        69 70 71  72  73 77 78  79  80  81 |
|  | GQT+<br>SEQ ID NO:6 | Mutant | CysGlyGlyGlySerValThrLeuAla<u>GlyGlnThr</u>ThrAsnAlaTyrValGlyGlyGly<br>                        69 70  71 72  73  74 75  76  77 78 |
| IL-2 | LDL+<br>SEQ ID NO:7 | Native | CysGlyGlyGlyGluHisLeuLeu<u>LeuAspLeu</u>GlnMetGlyGlyGly<br>                        15 16 17  18 19  20  21  22 23 |
|  | LDL−<br>SEQ ID NO:8 | Deleted | CysGlyGlyGlyGluHisLeuLeuGlnMetGlyGlyGly<br>                        15 16  17 18 22  23 |

[1]Each peptide was conjugated to the mouse Mab, RFB4 as described

Conjugation of the peptides to RFB4. All peptides contained an N-terminal cysteine residue to facilitate conjugation with maleimide-derivatized RFB4. RFB4 was treated with a 25-fold molar excess of succinimidyl 4-(N-maleimidemethyl)-cyclohexane-1-carboxylate and excess reagent was removed by gel filtration. The number of maleimide groups introduced into each molecule of RFB4 was determined by the backtitration of 2-mercaptoethylamine using Ellman's reagent (Husain and Bieniarz, 1994). The derivatized RFB4 was reacted with a 10-fold excess of the SH-peptide at room temperature for 4 hr and excess peptide was removed by dialysis against PBS. The maleimide reaction allowed the formation of the IgG1-C-S-peptide conjugate in which the number of peptide groups attached was similar to that of free maleimide groups.

As determined by both HPLC and radiolabeling, the RFB4-peptide conjugates (Table 3) contained 6 to 9 maleimide groups per molecule of IgG1 and these groups formed stable thioether bonds by reaction with the cysteine-containing peptides.

Effect of the RFB4-peptides on the morphology of HUVEC monolayers. To determine whether the LDV sequence in RTA and the LDL sequence in IL-2 damage HUVECs, monolayers were incubated with different concentrations of RFB4-RTA-peptides, RFB4-IL-2-peptides or controls. HUVECs were isolated, cultured and studied microscopically (Baluna et al., 1996; Soler-Rodriguez et al., 1993).

HUVEC monolayers were incubated at 37° C. for 18 hr with $10^{-6}$ M RFB4-LDV$^+$, RFB4-LDV$^-$, RFB4-GQT, RFB4-LDL$^+$, RFB4-LDL$^-$ or medium-only and then examined by phase-contrast microscopy (magnification 20×). Normal monolayers consisted of highly packed cells with elogated shapes whereas damaged cells rounded up and detached from the plate. Untreated HUVECs consisted of tightly packed elongated cells. Treatment with $10^{-6}$M RFB4-LDV$^+$ or RFB4-LDL$^+$ caused cell rounding after 2 hr of incubation and the formation of gaps in the monolayer after 18 hr. Toxic effects on HUVECs were not observed using RFB4-LDV$^-$, RFB4-GQT, or RFB4-LDL$^-$. The toxic effect of RFB4-peptides containing LDV or LDL were dose-dependent and comparable to the effects observed using RFB4-dgRTA (Table 4). These results indicate that the LDV sequence in RTA and its LDL homologue in IL-2 are involved in the EC toxicity of these agents.

TABLE 4

Effect of different concentrations of the RFB4-peptide constructs on the morphology of HUEC monolayers[1]

| | Concentration (M)[2] | | | |
|---|---|---|---|---|
| | $10^{-6}$ | $10^{-7}$ | $10^{-8}$ | 0 |
| RFB4-RTA-derived peptides | | | | |
| RFB4-LDV+ | ++ | ++ | + | – |
| RFB4-LDV– | – | – | – | – |
| RFB4-GGT+ | – | – | – | – |
| RFB4-IL-2-derived peptides | | | | |
| RFB4-LDL+ | ++ | ++ | + | – |
| RFB4-LDL– | – | – | – | – |
| RFB4-dgRTA | ++ | + | + | – |
| RFB4 | – | – | – | – |

[1]HUVECs were grown to confluence in 96-well tissue culture plates and cells were treated for eighteen hours with different concentrations of RTA-derived peptide-constructs in M199 with 2% FCS.
[2]The morphological changes were score as "–" no changes, "+" rounding up of cells and "++" disruption and detachment of cells from the cell monolayer.

In vivo effect of the RFB4-peptides. Although the vascular toxicity of IL-2 has been observed in experimental animals (Orucevic and Lala, 1995; Puri et al., 1989; Puri and Rosenberg, 1989; Rosenstein et al., 1986), it has been difficult to induce dgRTA-IT-mediated systemic manifestations of VLS in mice, rats or monkeys (Soler-Rodriguez, 1992). A model has been developed to study the effect of ITs on human endothelium in vivo by grafting vascularized human skin onto SCID mice, injecting the mice with dgRTA-ITs and measuring fluid accumulation in the graft as the wet/dry weight ratio (Baluna et al., 1998). Fluid accumulation in the human skin was measured by weighing punch biopsies of the skin grafts before and after freeze drying. This model was used to evaluate the effect of RFB4-LDV$^+$, RFB4-GQT$^+$, and RFB4-dgRTA in vivo (FIG. 1A).

The fluid accumulation in the lungs of normal SCID mice was also evaluated as IL-2 induces fluid accumulation in the lungs of mice (Orucevic and Lala, 1995). The water content of the lungs or skin grafts was calculated as the wet/dry weight ratio.

Figure 1B:
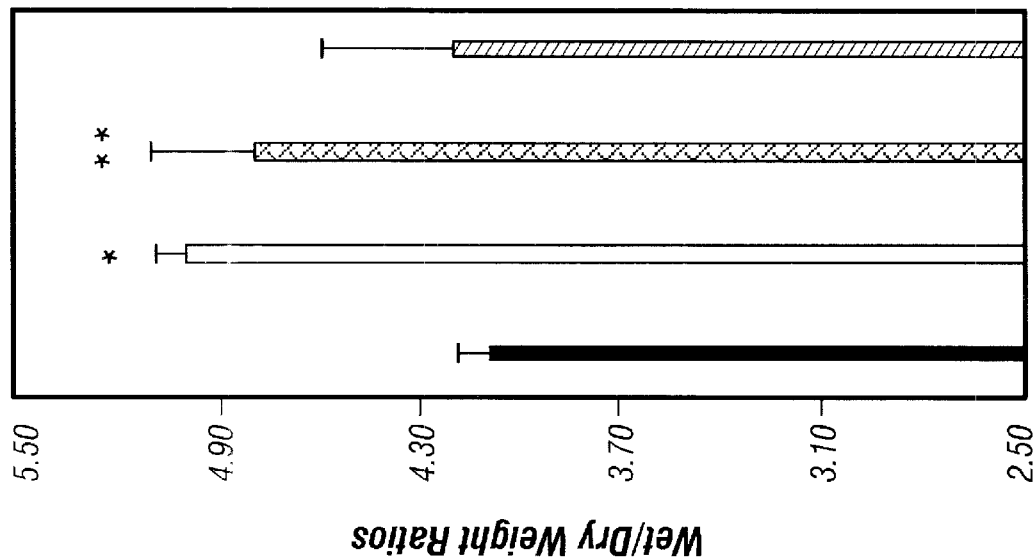

Although it has been difficult to demonstrate systemic manifestations of VLS in mice injected with RTA-ITs, vascular leak occurs in human skin xenografts in SCID mice. Increases in the wet/dry weight ratio of the human skin grafts after injection of RFB4-LDV$^+$ and RFB4-dgRTA were found but not after injection of RFB4-GQT$^+$. The fluid accumulation in these xenografts was comparable using either RFB4-dgRTA or RFB4-LDV$^+$. Comparable results were obtained using SCID mouse lungs (FIG. 1B). It should be noted that although the difference in the Figures may appear small, they are statistically significant and consistent with reports using IL-2 (Orucevic and Lala, 1995).

Flow cytometric analysis of the binding of dgRTA and RFB4-peptides to (x)D(y) sequence or at least one flanking residue. It is also contemplated that peptides or HUVECs. The fact that RFB4-LDV$^+$ and RFB4-LDL$^-$ damage HUVECs, implies that these peptides interact with a binding site on HUVECs, although, in the intact IL-2 or RTA molecules, the (x)D(y) motif may not be the primary binding site for ECs. To address these issues with toxins, a series of binding and binding/inhibition studies were carried out.

The proteins were coupled to fluorescein isothiocyanate (FITC) (Sigma, St. Louis, Mo.). $10^5$ HUVECs were washed twice in cold PBS containing 1% bovine serum albumin (BSA) and 0.01% sodium azide (PBS/BSA/AZ), resuspended in 100 ul of the same buffer and incubated with FITC-reagents for 30 minutes on ice in the dark, washed three times with PBS/BSA/AZ, fixed in 0.5 ml of 1% paraformaldehyde PBS/AZ, and analyzed using a FACScan (Becton Dickinson, Mountain View, Calif.) and the CytoQuest software.

The binding of dgRTA, PE38-lys and RFB4-peptides to HUVECs was examined. $10^5$ HUVECs were incubated on ice for 30 min with FITC-reagents in 100 μl PBS/BSA/AZ at varying, concentrations, washed, fixed in 1% paraformaldehyde and analyzed by flow cytometry. The values represent the mean±SD of three experiments using FITC-dgRTA, FITC-PE38-lys, and FITC-carbonic anhydrase as a control. Histograms of flow cytometric analyses of the binding of dgRTA, PE38-lys and carbonic anhydrase to HUVECs were made. The binding of FITC-RFB4-LDV⁺ (▲), FITC-RFB4-LDV⁻, FITC-RFB4-GQT⁺, FITC-RFB4, FITC-RFB4-LDL⁺, and FITC-RFB4-LDL⁻ were also evaluated. Histograms of RFB4-LDV⁻, RFB4-LDL⁺ and RFB4 were also made. The results of this study demonstrated that the 50% of maximal binding of FITC-dgRTA and FITC-PE38-lys required 0.035 μg and >100 μg/$10^5$ cells, respectively, demonstrating that dgRTA has a >3 log higher relative binding affinity for HUVECs than PE38-lys. This may be due to the fact that the LDV receptor on HUVECs has a lower affinity for homologous sequences in PE38-lys and/or that LDV in RTA, is more exposed. It is also possible that other non-homologous sequences in RTA (but not in PE38-lys) bind to HUVECs. The difference between the relative binding affinity of FITC-dgRTA (0.035 μg/$10^5$ cells/100 μl) and FITC-RFB4-LDV⁺ (0.5 μg/$10^5$ cells/100 μl) was only 2-fold if calculated on molar basis. Since the RFB4-peptide conjugates with deleted or mutated LDV sequences did not bind to HUVECs, the (x)D(y) motif is clearly involved in the binding.

Inhibition of the binding of dgRTA and RFB4-peptides to HUVECs. To provide further evidence for the role of the (x)D(y) motif in the binding of RTA to HUVECs, a series of binding inhibition studies were carried out. FITC-dgRTA or FITC-RFB4-LDV⁺ at concentrations representing 20–50% of maximal binding (0.035 μg/$10^5$ cells for dgRTA and 1.0 μg/$10^5$ cells for RFB4-LDV⁺) were incubated with HUVECs in the presence or absence of a 100-fold excess of dgRTA (Inland Laboratories, Austin, Tex.), RFB4-LDV⁺, RFB4, Fn (GIBCO Laboratories, Grand Island, N.Y.) or PE38-lys (NCI, Bethesda) for 30 min on ice in the dark. Washed cells were fixed in 1% paraformaldehyde and analyzed on the FACS.

Figure 2A:
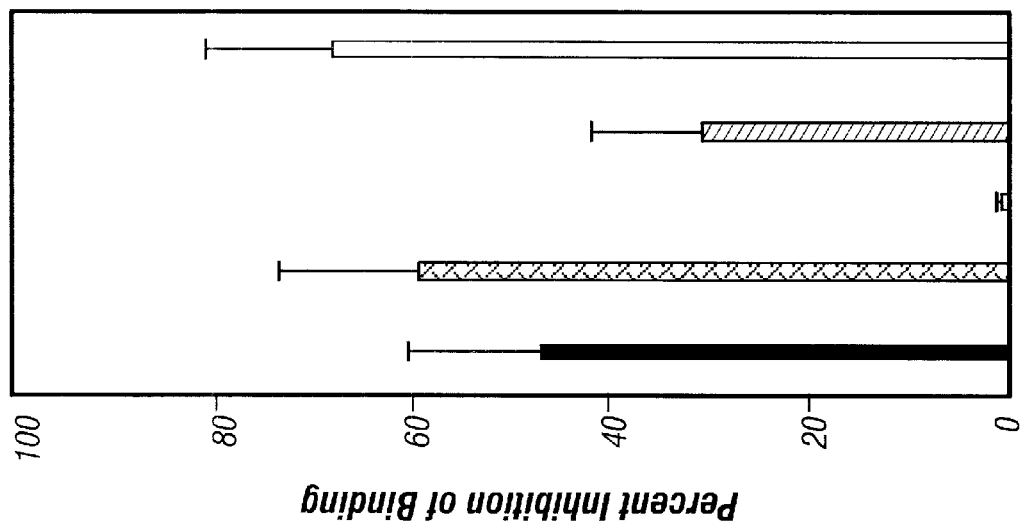
FIGS. 2A and 2B. Inhibition of the binding of dgRTA and RFB4-LDV+ to HUVECs.
Figure 2B:
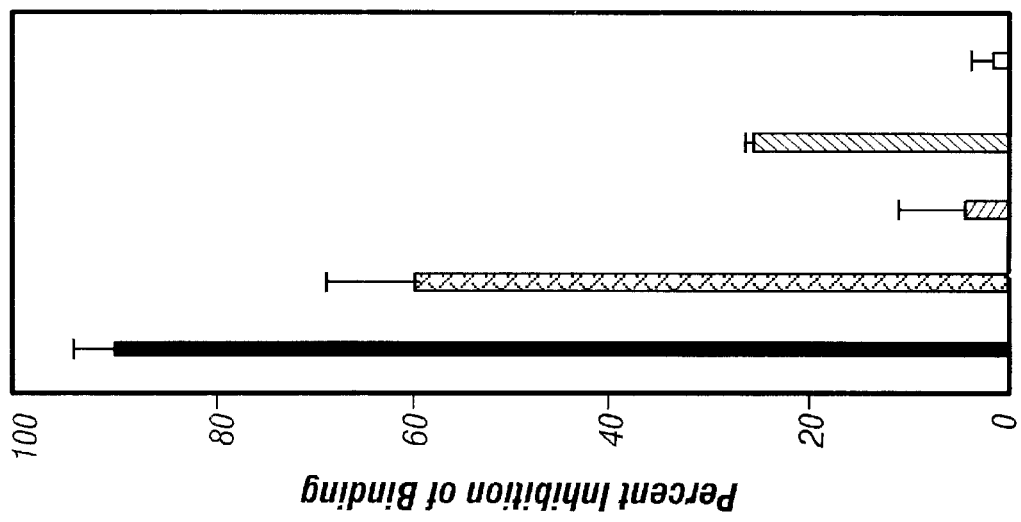
Figure 3:
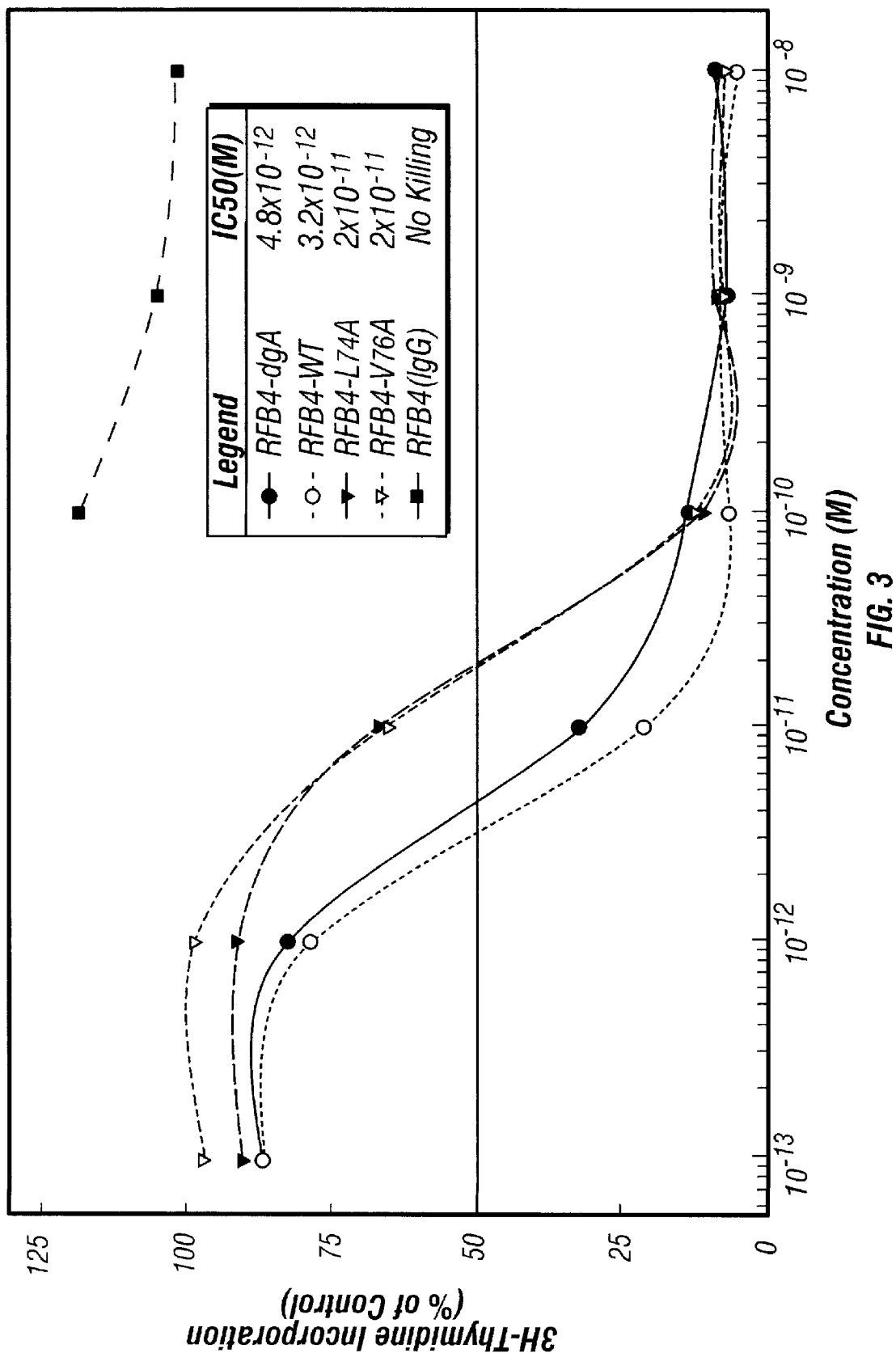
FIG. 3. RFB4-rRTA ITs $IC_{50}$ determinations. Selected examples of $LD_{50}$ determinations by in vitro cytotoxicity assays, where $IC_{50}$ is calculated as the concentration of IT at which [³H] leucine incorporation was inhibited by 50% relative to untreated control Daudi cell culture.
Figure 5B:
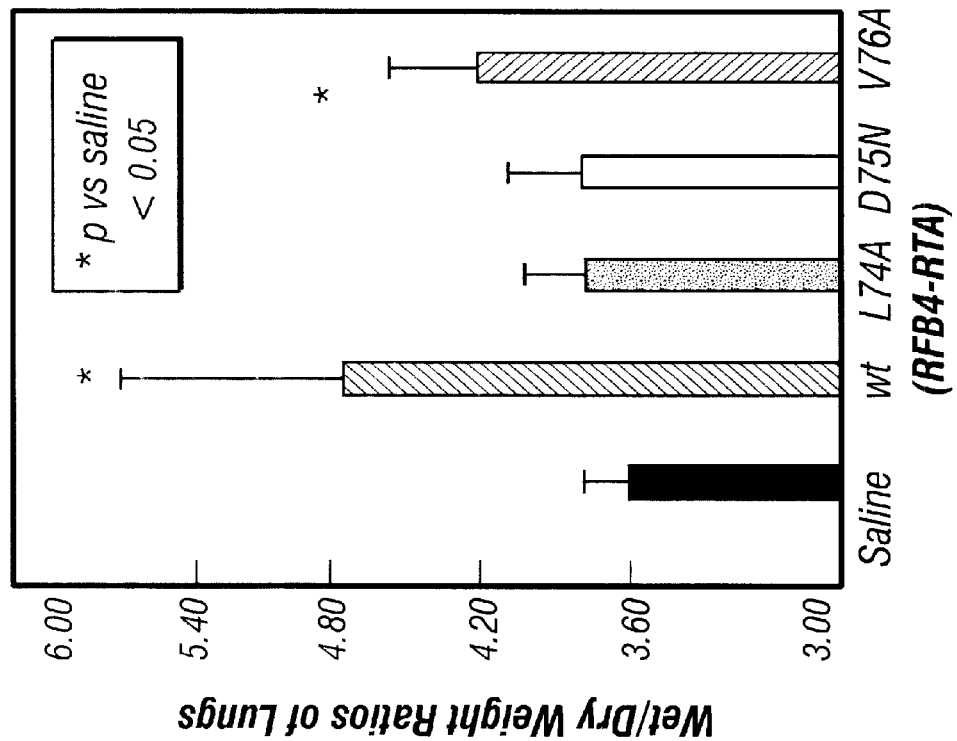
FIGS. 5A and 5B. In vivo effect of RFB4-rRTA ITs. SCID mice were injected with 200 µg of RFB4-rRTA ITs of saline.
Figure 5A:
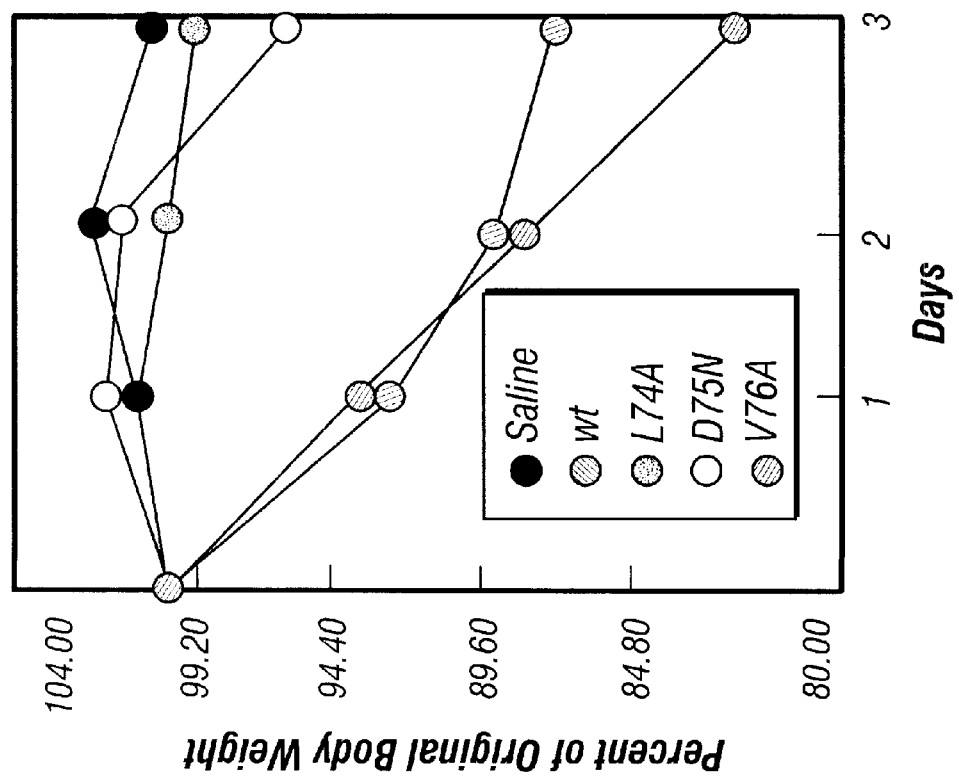
Figure 6:
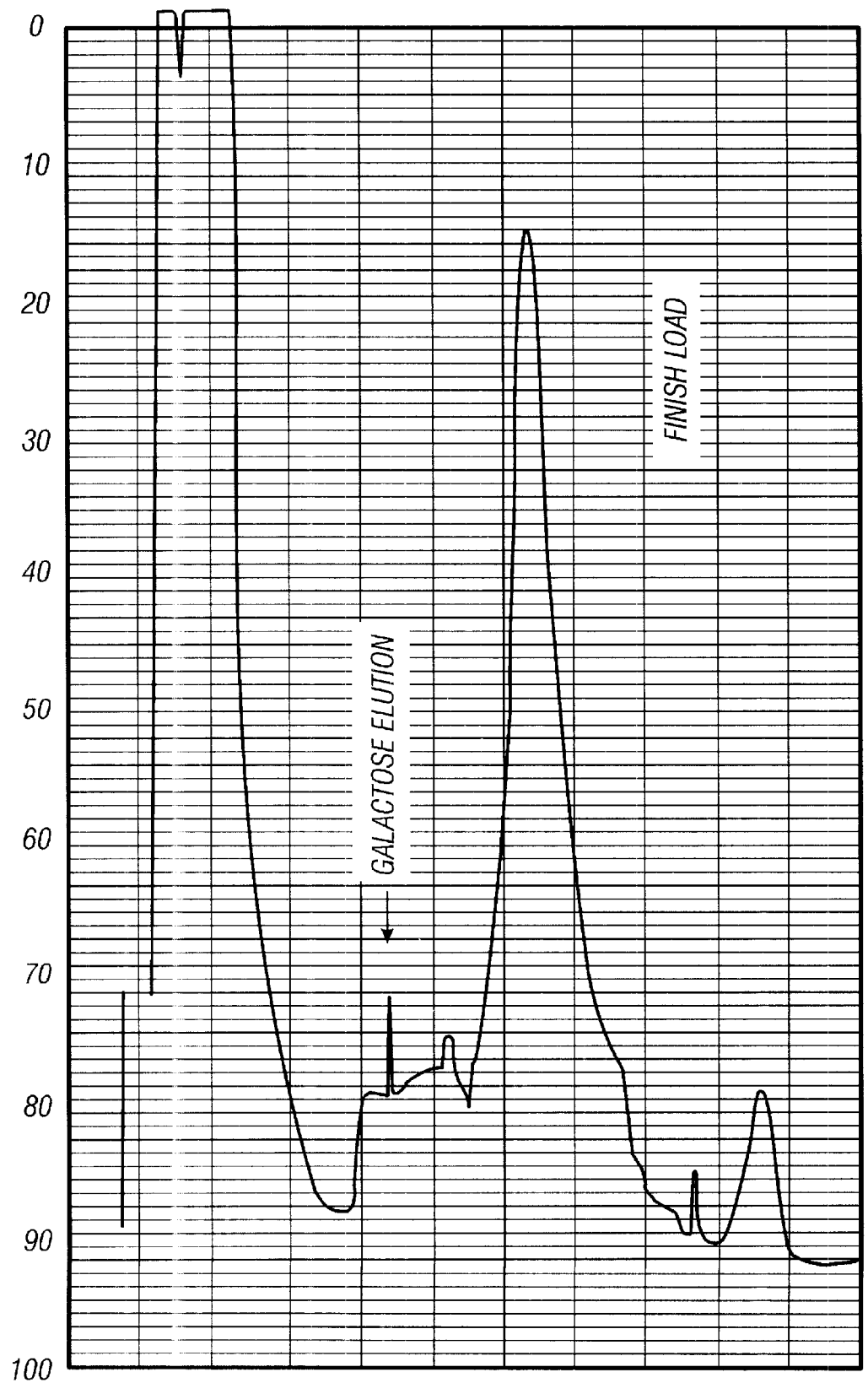
FIG. 6. Profile of Acid-Treated Sepharose 4B Column-Purification of Ricin
Figure 7:
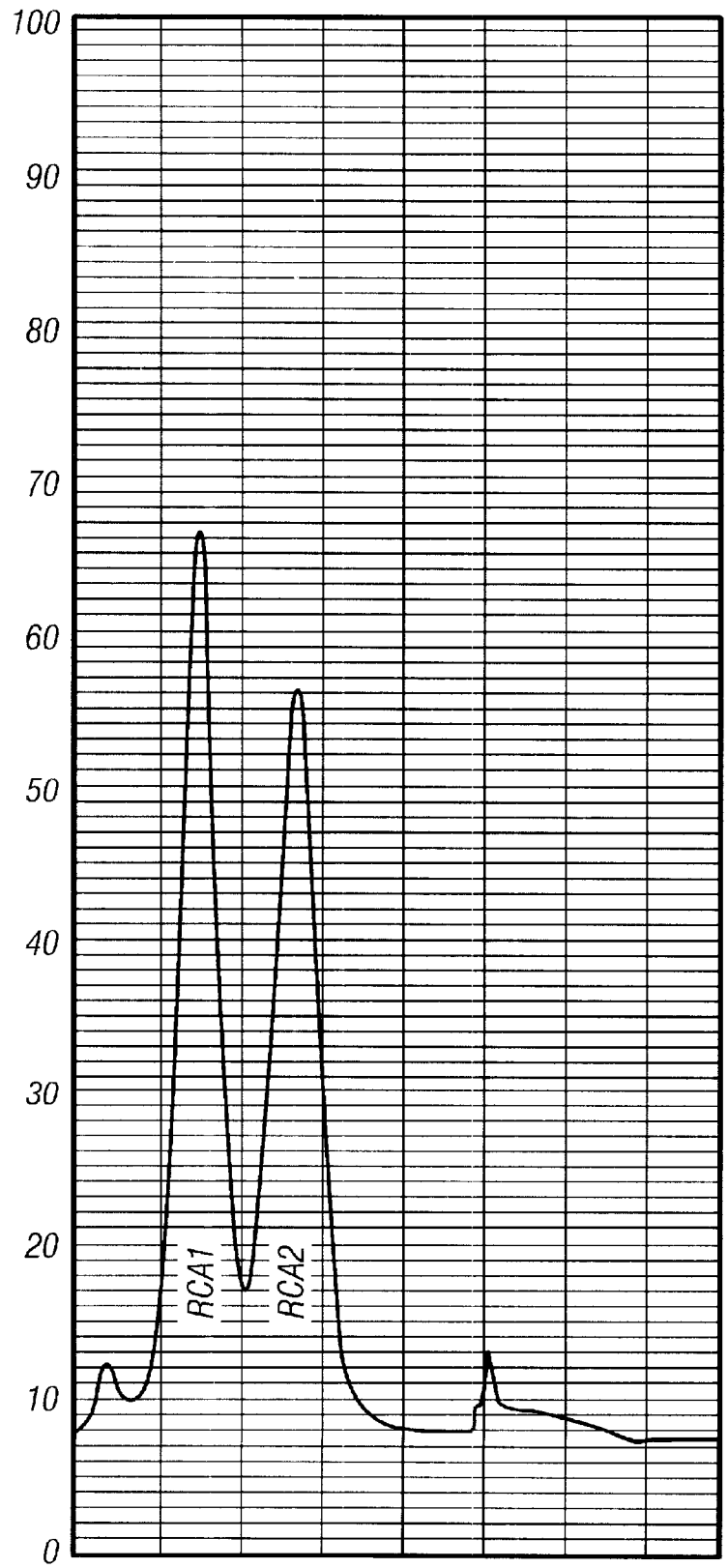
FIG. 7. Profile of Sephacryl S-200 Column-Separation of RCA-1 and RCA-2.
Figure 8:
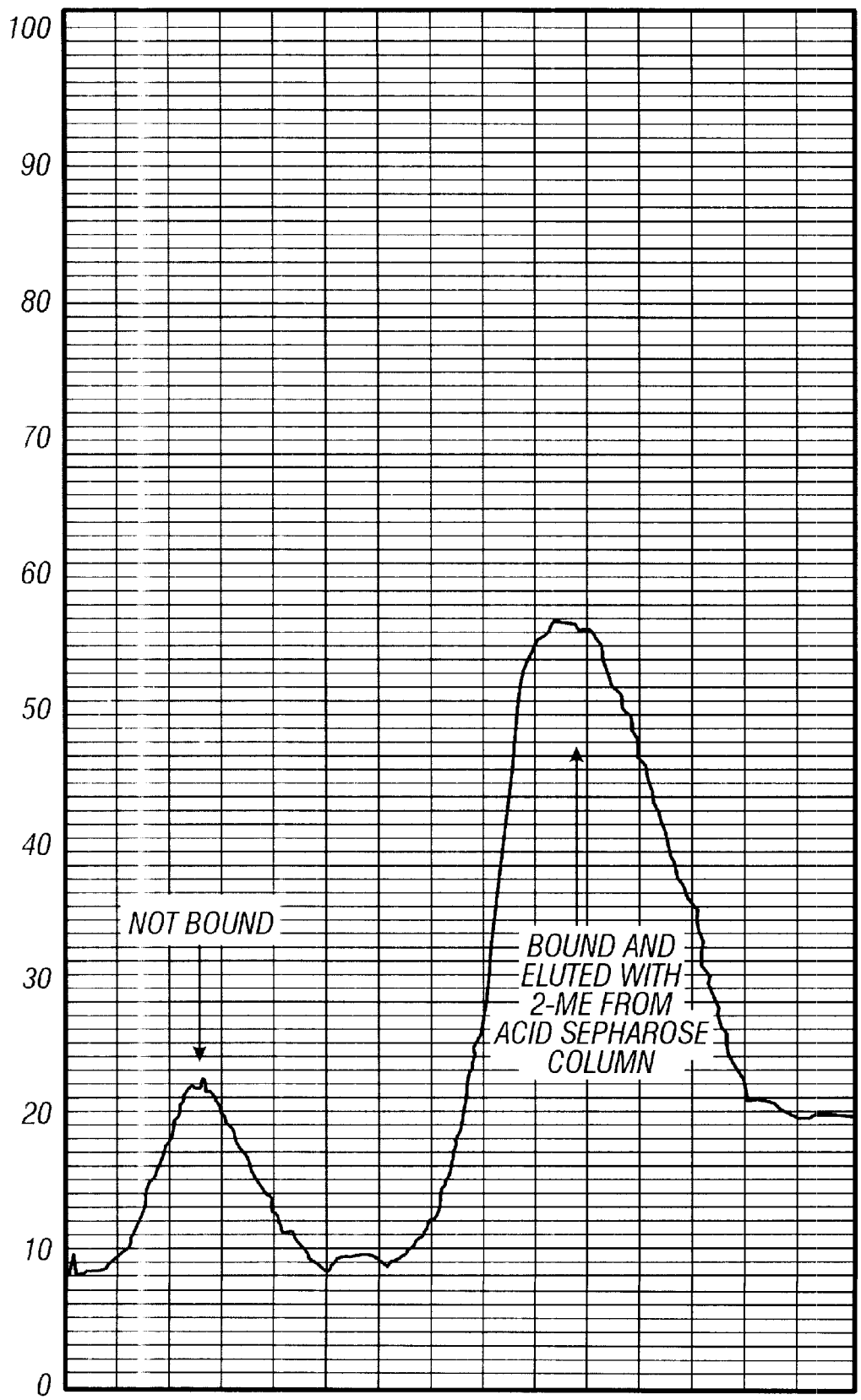
FIG. 8. Profile of DEAE Sepharose Column and Acid-Treated Sepharose 4B Column-Separation of dgRTA and DGRTB Chains.
Figure 9:
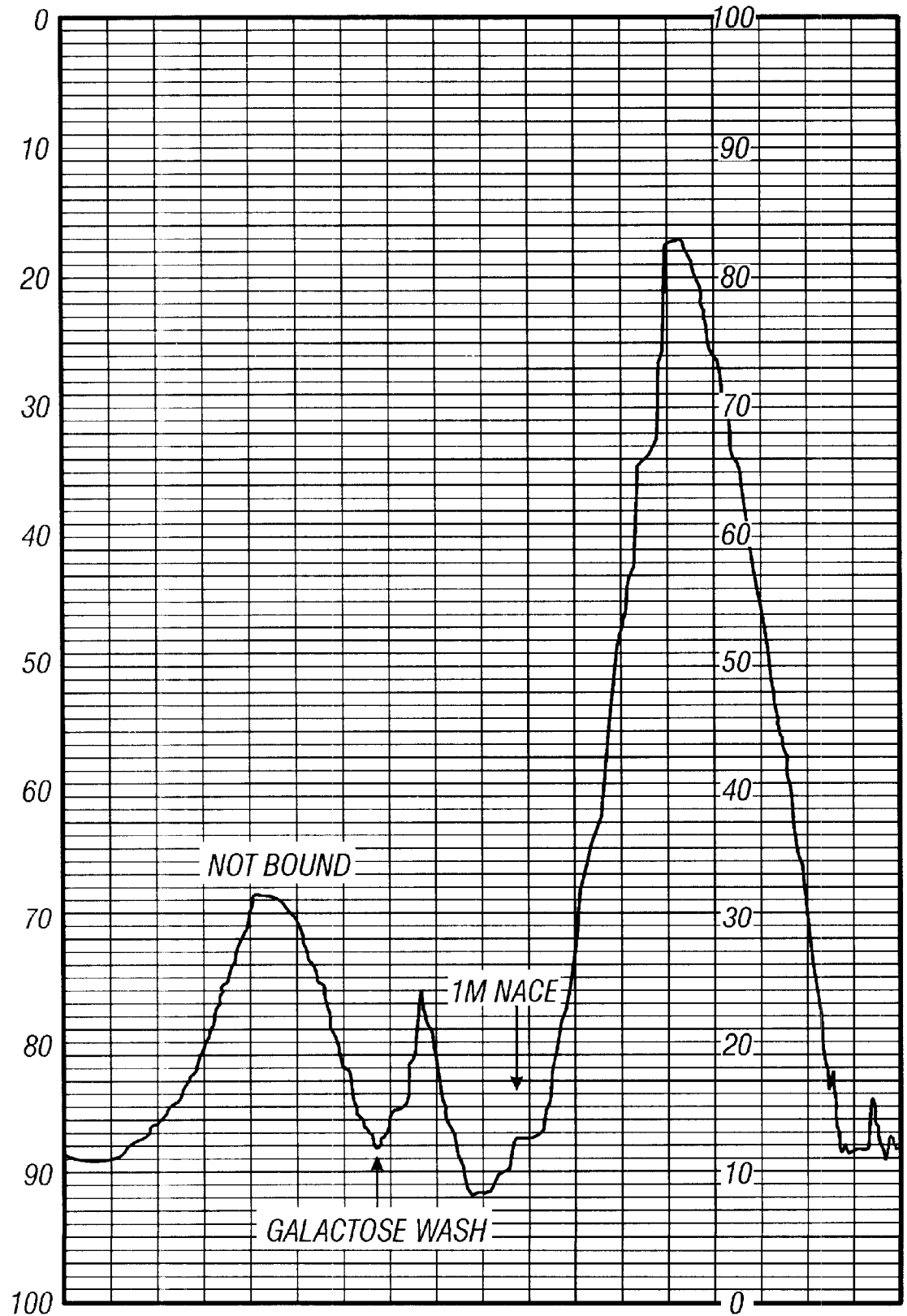
FIG. 9. Profile of Blue-Sepharose CL-4B Column—Purification of dgRTA.
Figure 10:
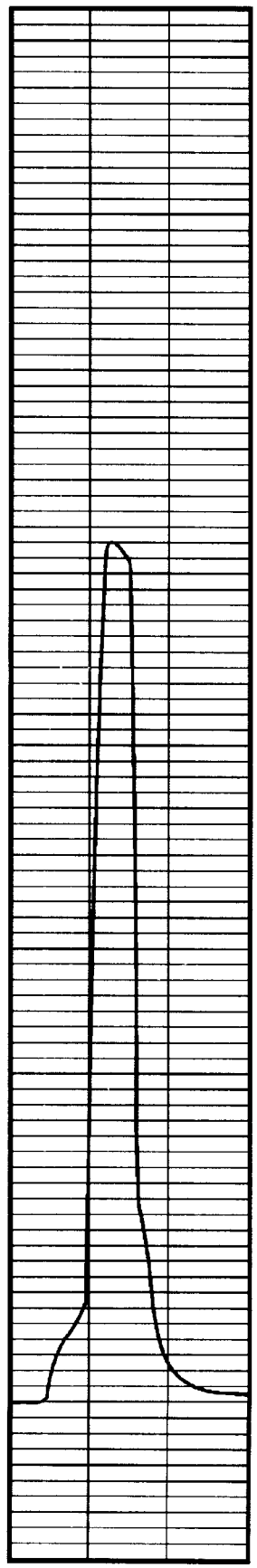
FIG. 10. Profile of Asialofetulin-Sepharose Column—Purification of dgRTA.

It was found that the binding of FITC-dgRTA to HUVECs was inhibited by >90% by dgRTA and by >60% by RFB4-LDV⁺ indicating that the binding of dgRTA is specific and that it involves, at least in part, the LDV sequence (FIG. 2A). The fact that the homologue-containing PE38-lys could not inhibit the binding of dgRTA (FIG. 2A) may be due to the fact that its relative affinity for HUVECs is more than three logs lower. In addition, dgRTA may have additional non-homologue binding sites for HUVECs, as suggested by the fact that RFB4-LDV⁺ inhibited its binding by 60% and not 100%. Furthermore, in the reverse studies, both dgRTA and RFB4-LDV⁺ inhibited the binding of FITC-RFB4-LDV⁺ to HUVECs to a similar extent (FIG. 2B), further indicating that the LDV sequence in RTA is involved in binding to HUVECs. Surprisingly, PE38-lys very effectively inhibited the binding of FITC-LDV⁺ to HUVECs (FIG. 2B) indicating that one or more of its LDV homologue sequences can compete with the LDV motif for binding of an LDV-containing peptide. It is contemplated that one or more homologue sequences in PE38-lys (GDL-348–350; GDV-430–432; or GDL-605–607) bind to and damage HUVEC. Fn also inhibited the binding of both FITC-dgRTA (FIG. 2A) and FITC-RFB4-LDV⁺ (FIG. 2B) to HUVECs, but it did so less effectively. In this regard, although Fn also contains the LDV motif, it has different flanking residues which may play a role in the availability of its LDV motif.

The data described above demonstrates that peptides containing the LDV motif in RTA and the LDL motif in IL-2, when attached to the RFB4 MAb specifically bind to and damage HUVECs in vitro. The IgG-peptide conjugates and the IgG-RTA IT were equally effective in inducing endothelial cell damage and increased vascular permeability in all three models.

The LDV sequence in RTA may be responsible for the initiation of events leading to VLS-like symptoms in vivo since injection of RFB4-RTA-peptides containing the native, but not mutated or deleted, LDV sequence caused vascular leak in lungs and in human skin xenografts in a manner analogous to that of the RFB4-dgRTA IT. dgRTA utilizes its LDV sequence, at least in part, to bind to HUVECs since peptides or proteins containing this motif inhibited the dose-dependent, saturable binding of RTA to HUVECs.

The stereoviews of LDV in RTA and LDL in IL-2 indicate that these motifs are partially exposed and should interact with cells. For RTA, this is supported by its dose dependent, saturable binding to HUVECs in vitro. Since the binding of RFB4-LDV⁺ to HUVECs could be partially inhibited not only by dgRTA but also by proteins containing LDV or LDV-homologues, i.e. Fn and PE38-lys, this further indicates a functional conservation in the (x)D(y) motif in several divergent molecules. Deletions or mutations in this sequence or the use of non-damaging blocking peptides may increase the therapeutic index of both IL-2 as well as ITs prepared with a variety of plant or bacterial toxins.

EXAMPLE 2

Reduced Pulmonary Vascular Leak in Mice

In this example, it was demonstrated that the enzymatic site or the putative VLS-inducing site in RTA can be mutated without effecting the activity of the other site. The results showed that an active site mutant (E177D) induces EC damage and pulmonary vascular leak while one particular LDV mutant (L74A) makes an active IT but does not induce this damage. Thus, a single amino acid change (L74A) yields an RTA with the desirable properties of IT activity with reduced vascular damage. These results demonstrate that it is now possible to generate an effective RTA-containing IT which does not cause VLS.

Plasmids and mutagenesis. It has been shown that E177 in RTA is one of several amino acids involved in the active site and that an E177D mutant has greatly reduced enzymatic activity. The pKK223 plasmid with (wt RTA gene) and the pUC 18 plasmid (E177D), both under IPTG-inducible control (O'Hare et al., 1987; Simpson et al., 1995). In addition, from the (wt)RTA construct, the RTA mutants with conserved changes in the LDV sequence were generated. All DNA manipulations were performed using standard techniques (Sambrook et al., 1989). Mutations were introduced into the wt sequence using QuikChange® (Stratagene) and mutagenic primer pairs as shown in Table 5. These mutants included L74A, D75N, D75A, D75E and V76A.

TABLE 5

Mutants and Primers

| Designation | Amino Acid Sequence[1] | Designation | Mutagenic Primer Sequences[2] |
|---|---|---|---|
| Wt SEQ ID NO:9 | LeuAla<u>LeuAspVal</u>ThrAsnAlaTyrValVal | | |
| L74a SEQ ID NO:10 | LeuAla<u>AlaAspVal</u>ThrAsnAlaTyrValVal | SEQ ID NO:15 | CTTTCTGTTACATTAGCCGCGGATGTCACCAATGCATATG |
| D75A SEQ ID NO:11 | LeuAla<u>LeuAlaVal</u>ThrAsnAlaTyrValVal | SEQ ID NO:16 | GTTACATTAGCCCTGGCTGTCACCAATGCATATG |
| D75E SEQ ID NO:12 | LeuAla<u>LeuGluVal</u>ThrAsnAlaTyrValVal | SEQ ID NO:17 | CTGTTACATTAGCCCTGGAAGTCACCAATGCATATG |
| D75N SEQ ID NO:13 | LeuAla<u>LeuAspVal</u>ThrAsnAlaTyrValVal | SEQ ID NO:18 | CTGTTACATTAGCCCTGAACGTCACCAATGCATATGTGG |
| V76A SEQ ID NO:14 | LeuAla<u>LeuAspAla</u>ThrAsnAlaTyrValVal | SEQ ID NO:19 | GTTACATTAGCCCTGGATGCTACCAATGCATATGTGGTC |

Expression of RTA in *E coli*. Overnight cultures of *E. coli* strain XL1-Blue freshly transformed with either plasmid in Terrific Broth (Sambrook et al., 1989) containing 100 μg/mL ampicillin at 37° C. were used to inoculate (1%) 500 mL of the same media (in 2 L flasks). Cultures were grown at 30° C. with vigorous shaking until they had reached an $OD_{600}$ of 0.6 to 0.8. Expression was induced using 0.3 mM IPTG and the cultures allowed to grow overnight (~15 h). Scaled up expression was carried out in a 5 L fermentor (New Brunswick Scientific, Edmon, N.J.) with the same media and inoculum as above. Cultures were grown with agitation of 400 rpm and airflow of 4.0 L/min at 37° C. until $OD_{600}$ of 0.5. The cultures were slowly cooled to 30° C., induced with 1.0 mM IPTG, and grown 16–18 h with agitation of 250 rpm and airflow of 2.5 L/min. Cells were harvested and resuspended in 10 mL PBS (50 mM phosphate-buffered saline, pH 7.0) and lysed by sonication (six 30-second bursts) or by passage through a French Press (Spectronic Instruments). Cell debris was removed by centrifugation at 15K rpm for 20 min; supernatants were filtered (0.2 μm) and stored at −20° C. until purification.

Radioimmunoassay (RIA) and bioassay of expressed RTA. The yield of expressed RTA was assayed using a solid phase RIA. In this assay wells of microtiter plates are coated with an affinity purified rabbit anti-RTA. Plates are washed and blocked with BSA. Dilutions of purified rRTA (standard curve) or of sample are added for 2 hrs at 25° C. Plates are washed and 100,000 cpm of $^{125}S$ affinity purified rabbit anti-RTA is added to each well for 1 hr at 25° C. Plates are washed. Wells are cut out and counted on a gamma counter. Concentration of rRTA in the samples are determined from the standard curve. Briefly, 96-well plates were coated with polyclonal rabbit anti-RTA, blocked with fetal calf serum, and serial dilutions of either the dgRTA or wt RTA standard or dilutions of the rRTA-containing *E. coli* lysates were added. Wells were washed and bound RTA was detected using $^{125}I$-labelled rabbit anti-RTA. The amounts of RTA in the *E. coli* extracts were determined from the standard curve.

Purification of rRTAs. rRTAs were purified from the bacterial lysates by ion-exchange chromatography on CM-Sepharose fast flow (Pharmacia). pH 6–9 proteins were eluted using a 0–300 mM NaCl gradient. Pooled fractions, comprising the main protein peak typically contained 50–80% rRTA. This pool was further purified by chromatography on Blue-Sepharose CL-4B; bound rRTA was eluted with 1 M NaCl (Ghetie et al., 1991). The RTA preparations were concentrated to 3–4 mg/mL and stored at −20° C. in 50% glycerol. Purified recombinant (r) RTA preparations were evaluated by sodium dodecyl sulfate polyacrylamide gel electrophoresis (SDS-PAGE) and were >90% pure. The enzymatic activity of wt rRTA, dgRTA and the mutant rRTAs was determined using a cell-free rabbit reticulocyte assay (Press et al., 1988).

Preparation of RFB4-RTA. The murine Mab, RFB4 (anti-human-CD22) was chemically conjugated to rRTAs and dgRTA using N-succinimidyl-oxycarbonyl-α-methyl-α (2-pyridyldithio) toluene (SMPT, Pierce) and purified as described previously for dgRTA (Ghetie et al., 1991; Knowles and Thorpe, 1987). The enzymatic activity of the RTA in the ITs was tested in the cell-free rabbit reticulocyte assay, following reduction (Press et al., 1988).

In vitro cytotoxicity assays. The cytotoxic activities of the different RFB4-containing-ITs were determined using $CD22^+$ Daudi cells and [3H]-leucine incorporation as described previously (Ghetie et al., 1988). The concentration of IT which reduced [$^3$H]-leucine incorporation by 50% relative to an untreated control culture was defined as the $IC_{50}$.

As shown in Table 6, when tested in the reticulocyte assay, the wt RTA and dgRTA had very similar activities although the wt RTA was slightly more active. Following coupling to the RFB4 Mab, dgRTA was approximately 3-fold less toxic than wt RTA. In contrast, the E177D rRTA and the RFB4-E177D IT were 3200 fold and 560 fold less enzymatically activite, respectively, in the reticulocyte assay and greater than $5\times10^7$ fold less toxic in the Daudi cell assay (Table 5 and FIG. 3). RFB4-EI77D, which bound to Daudi cells as effectively as RFB4-wtRTA, was virtually inactive as an IT.

TABLE 6

The Enzymatic Activity of rRTAs and ITs prepared with these rRTAs

| RTA | Fold decrease in activity of RTA vs wt RTA | Cell Free Reticulocyte Assay Fold decrease in activity vs wt RFB4-RTA | Daudi Cytotoxicity Assay Fold decrease in activity vs wt RFB4-RTA |
|---|---|---|---|
| wt | —[a] | —[b] | —[c] |
| DgRTA | 1.3 ± 0.6 (8)[d] | 3.0 ± 1.1 (6) | 4.4 ± 1.6 (19) |
| L74A[e] | 1.5 ± 0.4 (3) | 1.2 ± 0.8 (3) | 9.1 ± 5.3 (4) |
| D75N[e] | 13.5 ± 6.6 (4) | 5.5 ± 1.4 (4) | 660 ± 270 (3) |
| D75A[e] | 3.1 ± 1.7 (3) | 4.0 ± 2.8 (4) | 370 ± 240 (4) |
| D75E[e] | 5.1 ± 2.1 (3) | 12.2 ± 10.3 (5) | 260 ± 200 (5) |
| V76A[e] | (in progress) | 2.7 ± 1.6 (2) | 5.5 ± 3.2 (4) |
| E177D[e] | 3200 ± 1100 (3) | 560 ± 450 (5) | $5.0 \times 10^7$ (8)-- |

With regard to the LDV mutants, as compared to wt RTA, L74A was 1.2–1.5 less active in the reticulocyte assay and 6–9-fold less active as an IT in the Daudi cell cytotoxicity assay (Table 6 and FIG. 3). As compared to dgRTA, the L74A IT was 4–5-fold less active in the Daudi assay. Similar decreases were observed using V76A (Table 6). In contrast to both the L74A and V76A mutants, D75A, D75E and D75N were 3–13-fold less active in the reticulocyte assay, and >200 fold less active as ITs in Daudi cell cytotoxicity assays. This result indicated that D75 may be particularly important for internalization, for routing, or for intracellular stability of the RTA in Daudi cells. As compared to the wtRTA, L74A and V76A formed the most active IT.

Vascular toxicity of RFB4-rRTA. As a first step in evaluating the ability of ITs prepared with mutants RTAs to induce vascular damage, a series of in vitro studies using HUVECs were conducted. For in vitro assays, the effect of RFB4-rRTA on the morphology of HUVECs monolayers was tested as described previously (Baluna et al., 1996).

As shown in FIG. 4, the ITs containing wtRTA, dgRTA or the enzymatically inactive E177D RTA damaged HUVECs. Since E177D contains LDV, but has a disrupted active site and is inactive as an IT, this indicated that the active site of RTA and the putative VLS-inducing site (LDV) of RTA are distinct and that enzymatic activity does not appear to be the most important feature for the ability of RTA to damage HUVECs. In contrast, when ITs containing mutations in L, D or V (but not the active enzymatic site) were tested on HUVECs, only the IT containing V76A damaged these cells. Taken together with the results of the Daudi cell studies, the only IT which was active in the Daudi cell cytotoxicity assay and inactive in the HUVEC assay contained L74A. In contrast, ITs prepared with the D75 mutants had greatly reduced activity in the Daudi cytotoxicity assay even though there were not toxic to HUVECs. Conversely, the IT prepared with E76A, was active on Daudi cells, but damaged HUVECs. Of the ITs prepared with the 5 LDV mutants, the L74A mutant appeared to contain both of the desired properties in vitro.

For in vivo assays, the effect of RFB4 ITs was determined in the SCID/Daudi tumor model (Ghetie et al., 1992). Female SCID mice were injected I.V. (lateral tail vein) with $5\times10^6$ Daudi cells on day zero. ITs were injected I.V. on days 1, 2, 3 and 4. Groups of 5 mice were used for each treatment and studies were repeated. Treatment groups received (1) no treatment (control); (2) RFB4-dgRTA 40% of the LD50 or 60 $\mu$g/mouse; (3) RFB4-wt RTA, 40% of the LD50 or 80 $\mu$g; (4) RFB4 E177D, 40% of the LD50 or 400 $\mu$g/mouse; (5) RFB4 L74, 40% of the the LD50 or 200 $\mu$g/mouse; (6) RFB4 V76A. Mice were followed and sacrificed when the paralysis of their hind legs occurred. Pulmonary vascular leak in IT-injected SCID mice was evaluated as described (Baluna et al., 1999). The water content of the lungs was calculated as the wet/dry weight ratios of lungs removed from mice injected with 10 ug IT/g of mouse weight.

Unlike humans, mice injected with RTA-containing ITs do not manifest systemic VLS in terms of weight gain and edema but they do lose significant weight and show pulmonary vascular leak. SCID mice were injected with the ITs prepared with the mutant rRTAs and monitored both weight loss and pulmonary vascular leak. As shown in FIG. 5, when mice were injected with 10 ug IT/g of body weight, both weight loss (A) and pulmonary leak (B) were observed using the ITs prepared with dgRTA, wtRTA or V76A. In contrast, the ITs containing L74A D75A, D75N or D75E did not induce weight loss or pulmonary leak. At this dose, the RFB4-E177D IT did not cause weight loss but did induce pulmonary leak. These results further demonstrated that the IT containing L74A RTA possesses the desired properties. It is contemplated that weight loss is related primarily to the LDV sequence but that severe weight loss, as seen in the IT prepared with wt RTA, maybe related to both an active site and the LDV sequence of the RTA.

When coupled to RFB4, an active site mutant, E177D, induced EC damage and vascular damage in vivo although RFB4-E177D was $10^7$-fold less active than RFB4-wt RTA in vitro (i.e., it was inactive). A single amino acid change in RTA (L74A) resulted in the expression of a highly active RTA enzyme which made an effective IT both in vitro and in vivo. As compared to RFB4-dgRTA which have been used in mice and patients, RFB4-L74A was only 5-fold less active. At the same dose as RFB4-wt RTA, RFB4-L74A did not damage ECs or cause weight loss in mice. As an IT, it had an $LD_{50}$ which was 20-fold higher than that of an IT prepared with wt RTA, indicating that much higher doses should be safe in vivo. In contrast to RFB4-L74, ITs prepared with mutants containing alterations in D75, although enzymatically active, performed very poorly in the Daudi cytotoxicity assay. Hence D75 may be involved in internalization, intracellular routing or intracellular stability of the RTA. Additionally, a V76 mutant was both enzymatically active and active as an IT but also induced both EC damage and vascular damage.

Taken together, these studies clearly demonstrate that L74A is a desirable RTA mutant. Because RFB4-L74A has a much higher $LD_{50}$ in mice, it will now possible to refine dose regimens to determine whether the therapeutic window has been widened.

EXAMPLE 3

Production and Purification of DGRTA

Inland Laboratories has formally produced dgRTA. However, the following example describes a procedure for producing dgRTA for use in the present invention.

A powdered acetone extract of castor beans is the starting material. Ricin is extracted from this powder, the ricin is deglycosylated, separated into A and B chains, and the dgRTA is purified.

Bulk raw material, powdered acetone extract of castor beans, can be purchased from Sigma Bulk Chemical Sales. The material arrives in plastic bottles which have a 1.0 L capacity and contain 200 grams of powder. The bottles are stored in a locked cabinet until the procedure is initiated.

Table 7 lists the composition of the buffers and solutions needed for the procedure and Table 8 lists the specifications for the buffers and solutions. Table 9 lists the equipment used for the production and purification of dgRTA and Table 10 provides a summary of the steps and columns used in the procedure.

TABLE 7

COMPOSITION OF BUFFERS

| | |
|---|---|
| AA | 200 mM acetic acid adjusted to pH 3.5 with 1M NaOH |
| BB | 50 mM boric acid adjusted to pH 8.0 with 1M concentrated NaOH |
| BB + 1M NaCl | BB + 1M NaCl, pH 8.0 |
| BB + 0.2M galactose | BB + 0.2M galactose, pH 8.0 |
| Deglycosylation buffer | AA + 40 mM NalOQ, + 80 mM NaCNBH3, pH 3.5 |
| PBS | 50 mM H2NaPO4 + 150 mM NaCl adjusted to pH 7.2 with 1M NaOH |
| Reducing BB | BB + 4% mercaptoethanol, pH 8.0 |
| Tris | 2M Tris-HCI, pH 10.8 |

TABLE 8

BUFFER SPECIFICATIONS

| Buffer | Sterility | PH | Conductivity | Endotoxin |
|---|---|---|---|---|
| AA | Sterile | 3.5 | 0.9 mΩ | Zero |
| BB | Sterile | 8.0 | 5.0 mΩ | Zero |
| BB + 1M NaCl | Sterile | 8.0 | 60 mΩ | Zero |
| BB + 0.2M galactose | Sterile | 8.0 | 4.6 mΩ | Zero |
| Deglycosylation buffer | Sterile | 3.5 | 8.0 mΩ | Zero |
| PBS | Sterile | 7.2 | 11.5 mΩ | Zero |
| Reducing BB | Sterile | 8.0 | 5.0 mΩ | Zero |
| Tris | Sterile | 10.8 | 25 mΩ | Zero |

TABLE 9

EQUIPMENT

| |
|---|
| Amicon concentrator, Model #CH2 |
| Autoclave, Model Hirayama |
| Biological safety cabinet (hood), Model NuAire #NU-425-400 |
| Circulating shaker, Model Fisher #631 |
| 1μ Centrifuge; Model, Jovan #GR-412 |
| Centrifuge tubes description, IEC 750 ml |
| Gravity Connection Owen, Model Precision |
| Negative pressure refrigerator (a negative pressure, refrigerated, chromatography box), Model EJS #CR-84 |
| Pharmacia spectro ultrospec III |
| Technicloth TX 609 (from Tex Wipe) |
| Whatmann 90377A (1.0 p.m) capsule filter |

TABLE 10

COLUMN SPECIFICATIONS

| COLUMN | SIZE (CM) | BED VOLUME | EQUILIBRATION BUFFER | PROTEIN LOADED | VOLUME LOADED | ELUTION BUFFER | FLOW RATE |
|---|---|---|---|---|---|---|---|
| Acid-Treated Sepharose 4B | 25 × 15 | 7.36 L | BB | ~100,000 ODU | 4 L | BB + 0.2M galactose | 4.5 L/h |
| Sephacryl S-200 | 25 × 90 | 44.2 L | AA | ~7,000 ODU | 1.5 L | None | 4.5 L/h |
| Columns run in tandem: | 11 × 30 | 2.8 L | BB | 8,000 mg ricin toxin (RCA2) | 3.5 L | Reducing BB | 4.5 L/h |
| DEAE-Sepharose And Acid-Treated Sepharose 4B | 25 × 30 | 14.7 L | | | | | |
| Blue Sepharose CL-4B | 25 × 15 | 7.36 L | BB | 3,000 mg dgA | 30 L | BB + 1M NaCl | 1.5 L/h |
| Aslalofetuin-Sepharose | 11 × 30 | 2.8 L | BB | 2,000 mg dgA | 10 L | None | 1.5 L/h |

*All columns are kept in the negative refrigerator at 4° C.

Extraction of bulk ricin: Each extraction batch may consist of two bottles of the castor bean powder. These are opened in the biological safety cabinet (hood), and 1.0 L of PBS is added to each bottle. Each bottle is capped with the original lid, placed on the circular shaker in the hood, and shaken for 1 hour at 200 cycles/minute, at room temperature (RT). The bottles are placed at 4° C. for 30 min to allow for sedimentation of particulates. The supernatant from each bottle is poured into an intermediate vessel which has a cover and spout, and from that vessel, the liquid is poured into 750 ml plastic centrifuge bottles, both steps being performed in the hood. The centrifuge bottles are capped and wiped clean with moist paper towels before they are removed from the hood. The centrifuge bottles are placed in carriers in the centrifuge and centrifuged at 3,700 rpm for 20 minutes at 4° C. The centrifuge bottles are removed, taken to the hood and the supernatants are decanted and filtered through Technicloth TX609 paper into a 6 L Erlenmeyer flask.

A second extraction is performed. The sediment in the two factory bottles is resuspended with 1.0 L PBS and the extraction procedure including 1 h of shaking at RT followed by centrifugation and filtration is repeated.

Purification of ricin: All of the following procedures are performed in the negative pressure chromatography box at 4° C.

Both the first and second extractions are pooled and filtered through a Whatman 90377A (1.0 pm) capsule filter. The absorbance at 280 nm is determined and the total protein extracted from the powder is calculated and recorded.

The clarified supernatant is then pumped from the flask onto the acid-treated Sepharose 4B column. The unbound fraction is collected, autoclaved and discarded. The bound fraction is eluted with BB+0.2 M galactose. The eluate is collected directly into a CH2 Amicon concentrator and concentrated to 1.5 L. The concentrate is transferred to a flask and the volume is measured. An aliquot is used to measure the absorbance at 280 nm and the total protein in ODU is recorded.

The protein is pumped from the flask onto the Sephacryl S-200 column, equilibrated with AA. Separation of peak 1 (RCA1=ricin agglutinin) and peak 2 (RCA2=ricin toxin) is determined by the lowest absorbance at 280 nm between peak 1 and peak 2 (see FIG. 7).

The first peak contains ricin agglutinin and is discarded. The second peak contains ricin, it is collected directly into the Amicon concentrator and concentrated to 2.5 mg/ml. The volume, OD 280 and total amount of protein in mg is recorded. The ricin is pumped from the concentrator into a capped vessel, which is then wiped with moist paper towels and removed from the chromatography refrigerator.

Deglycosylation of ricin: The vessel containing the ricin solution is opened in the hood. An equal volume of deglycosylation buffer is added. The vessel is capped, wiped, and placed in the chromatography refrigerator for a 4 h incubation at 4° C. The vessel is then placed in the hood, opened, and glycerol is added to a final concentration of 1% in order to stop the reaction. The vessel is again capped, wiped, placed in the chromatography refrigerator and kept overnight at 4° C.

Separation of ricin A and B grains and purification of dgRTA: After overnight incubation, the vessel is removed from the refrigerator and placed in the hood. The vessel is opened and Tris is added until the pH reaches 8.0. The neutralized ricin solution is pumped into 2 columns connected together in tandem in the chromatography refrigerator. The first column contains DEAF-Sepharose and the second contains acid-treated Sepharose 4B. Both columns ate equilibrated with BB. The purpose of the DEAE—Sepharose column is to bind endotoxin. Once the absorbance at 280 nm of the effluent from the acid-treated Sepharose 413 column falls to 0.05 ODU (end of peak 1, FIG. 8), the ricin has gone through the DFAE Sepharose column and into the acid-treated Sepharose 4B column, where it is bound.

Peak 1 represents a small amount of dgRTA that does not bind to acid-treated Sepharose 4B. The columns are then separated and reducing BB is pumped into the acid-treated Sepharose 4B column until the absorbance at 280 nm equals the absorbance of the reducing BB (0.12 ODU). The pump is then stopped and the column is incubated for 4 hours at 4° C. During this time, the S-S bond between the ricin A and B chains is reduced which results in the separation of the two chains.

The ricin B chain remains bound to the acid-treated-Sepharose 413 column. The column is then washed with reducing BB and the free dgRTA is collected (peak 2, FIG. 8). The collection is stopped when the absorbance at 280 mn returns to the absorbance of reducing BB. The OD 280 of the collected effluent (dgRTA solution) is measured and the volume and protein concentration in ODU is recorded.

The acid-treated Sepharose 4B column is eluted with BB+0.2 M galactose and the eluted ricin B chain is discarded.

The dgRTA solution in reducing BB is then pumped over a column of Blue-Sepharose CL-4B equilibrated with BB and held at 4° C. The column is washed with BB until the absorbance at 280 nm drops to baseline. The column is then washed with BB+0.2 M galactose until the small peak is eluted (Peak 2) and the absorbance at 280 nm returns to the baseline value. This procedure is applied to remove all traces of whole ricin toxin (RCA2) or B chain that can interact with the Sepharose matrix. dgRTA is eluted from the Blue-Sepharose column with BB+1 M NaCI as shown in FIG. 9, Peak 3 and the volume and absorbance at 280 mn is measured and recorded.

The eluate is then pumped onto the Asialofetuin-Sepharose column equilibrated with BB and held at 4° C. The nonbound fraction, starting when the absorbance is over 0.05 ODU and ending when it returns 0.05 ODU, as shown in FIG. 10, is diafiltered in the Amicon concentrator to decrease the NeCI concentration to 0.25 M and to increase the protein concentration to 2 mg/ml. DTT is then added to a final concentration of 10 mM and the solution is filtered through a 0.22 μm filter. The reduced dgRTA solution is mixed with an equal volume of glycerol and stored at −20° C. The column is eluted with BB+0.2 M galactose and the eluate is discarded.

Testing and specifications: Table 11 lists the tests and specifications for dgRT.

TABLE 11

Tests and Specifications for dgRTA

| TEST MATERIAL | TEST | SPECIFICATION |
|---|---|---|
| DgRTA | Protein concentration | 2–3 mg/ml |
| | Sterility | Sterile |
| | Endotoxin by LAL | <5 EU/mg |
| | Purity by SDS gel | >95% of protein @28–33 Kda MW peak |
| | Con A binding | <20% bound |
| | $IC_{50}$ (reticulocyte assay) | 1–5 × $10^{11}$M |
| | $IC_{50}$ (Daudi cell assay) | 0.5–5 × $10^7$M |
| | $LD_{50}$ (BALB/c mice) | 15–30 μg/g |
| * | * | * |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

*Antibodies: A Laboratory Manual*, Cold Spring Harbor Laboratory, Cold Spring Harbor, N.Y., 1988.
Atherton et al., *Biol. of Reproduction*, 32, 155–171, 1985.
Azuma et al., "Correlation between augmented resistance to influenza virus infection and histological changes in lung of mice treated with trehalose-6,6'-dimycolate," *J Biol Response Mod.*7(5):473–482, 1988.
Baluna and Vitetta, "An in vivo model to study immunotoxin-induced vascular leak in human tissue," *J. Immunother.*, 1999 22(1):41–47, 1999.
Baluna and Vitetta, "Vascular leak syndrome: A side effect of immunotherapy," *Immunopharmacology*, 37:117–132, 1996.
Baluna et al., "Fibronectin inhibits the cytotoxic effect of ricin A chain on endothelial cells," *Int. J. Immunopharm.*, 18:355–361, 1996.
Berberian et al., Science, 261:1588–1591, 1993.
Blobel and White, "Structure, function and evolutionary relationship of proteins containing a disintegrin domain," *Curr. Opin. Cell Biol.*, 4:760–765, 1992.
Cleary et al., *Trends Microbiol.*, 4:131–136, 1994.
Clements et al., *J. Cell Sci.*, 107:2127–2135, 1994.
Collins et al., *Proc. Natl. Acad. Sci. USA*, 85:7709–7713, 1988.
Coulson et al., *Proc. Natl. Acad. Sci. U.S.A*, 94:5389–5394, 1997.
Cunningham et al., "High-resolution epitope mapping of hGH-receptor interactions by alanine-scanning mutagenesis," *Science* 244(4908):1081–1085, 1989.
De Jager et al., "Current status of cancer immunodetection with radiolabeled human monoclonal antibodies" *Semin Nucl Med* 23(2):165–179, 1993.
Dholakia et al., *J. Biol. Chem.*, 264, 20638–20642, 1989.
Doolittle M H and Ben-Zeev O, "Immunodetection of lipoprotein lipase: antibody production, immunoprecipitation, and western blotting techniques" *Methods Mol Biol.*, 109:215–237, 1999.
Downie et al., *Am. J. Respir. Cell Molec. Biol.*, 7:58–65, 1992.
Dubos et al., 1947.
Dutcher et al., *J. Clin.Oncol.*, 9:641–648, 1991.
Engert et al., In: *Clinical Applications of Immunotoxins*, Frankel (ed.), 2:13–33, 1997.
Freifelder, Physical Biochemistry, Second Edition, pages 238–246
Gefter et al., *Somatic Cell Genet.* 3:231–236, 1977.
Ghetie et al., "The GLP large scale preparation of immunotoxins containing deglycosylated ricin A chain and a hindered disulfide bond," *J. Immunol Methods*, 142(2):223–230, 1991.
Ghetie et al., *Cancer Res.* 48:2610, 1988.
Goding, In: *Monoclonal Antibodies: Principles and Practice*, 2d ed., Orlando, Fla., Academic Press, pp. 60–61, 65–66, 71–74, 1986.
Greenspoon et al., *Int. J. Pept. Res.*, 43:417–424, 1994.
Gulbis B and Galand P, "Immunodetection of the p21-ras products in human normal and preneoplastic tissues and solid tumors: a review" *Hum Pathol* 24(12):1271–1285, 1993.
Halling et al., "Genomic cloning and characterization of a ricin gene from *Ricinus communis*," *Nucleic Acids Res.* 13(22):8019–8033, 1985.
Huang, *Cellular and Molecular Life Sciences*, 54:527–540, 1998.
Hunter et al., "Adjuvant activity of non-ionic block copolymers. IV. Effect of molecular weight and formulation on titre and isotype of antibody," *Vaccine*. 9(4):250–256, 1991.
Husain and Bieniarz, *Bioconjug. Chem.*, 5:481–490, 1994.
Husson et al., "Gene replacement and expression of foreign DNA in mycobacteria," *J Bacteriol.* 172(2):519–524, 1990.
Inouye et al., "Up-promoter mutations in the lpp gene of *Escherichia coli*," *Nucl. Acids Res.*, 13:3101–3109, 1985.
Jackson et al., *J. Med. Chem.*, 40:3359–3368, 1997.
Jacobs et al., "Introduction of foreign DNA into mycobacteria using a shuttle phasmid," *Nature*, 327(6122):532–535, 1987.
Kang et al., *Science*, 240:1034–1036, 1988.
Khatoon et al., *Ann. of Neurology*, 26, 210–219, 1989.
King et al., *J. Biol. Chem.*, 269, 10210–10218, 1989.
Knowles, P. P. and Thorpe, P. E. *Anal. Biochem.*, 160:440, 1987.
Kohler and Milstein, "Continuous cultures of fused cells secretaring antibody of predefined specificity," *Nature*, 256:495–497, 1975.
Kohler et al., *Methods Enzymol.*, 178:3, 1989.
Kreier et al., Infection, Resistance and Immunity, Harper & Row, New York, (1991)).
Lamb et al., "Nucleotide sequence of cloned cDNA coding for preproricin," *Eur J Biochem*, 148(2):265–270, 1985.
Lazarus and McDowell, "Structural and functional aspects of RGD-containing protein antagonists of glycoprotein IIb-IIIa," *Curr. Opin. Cell Biol.*, 4:438–445, 1993.
Lenert et al., *Science*, 248:1639–1643, 1990.
Li et al., *Proc. Natl. Acad. Sci. USA*, 92:9308–9312, 1995.
Lotte et al., "BCG complications. Estimates of the risks among vaccinated subjects and statistical analysis of their main characteristics," *Adv Tuberc Res.* 21:107–193, 1984.
Lu et al., *J. Biol. Chem.*, 271:289–294, 1996.
Luelmo F., "BCG vaccination," *Am Rev Respir Dis.* 125(3 Pt 2):70–72, 1982.
Maeda et al., *Biochem. Biophys. Res. Commun.*, 241:595–598, 1997.
Makarem and Humphries, *Biochemical Society Transactions*, 19:380S–382S, 1991.
Martinet et al., "Transposition of an antibiotic resistance element in mycobacteria," *Nature*, 345(6277):739–743, 1990.
McLane et al., *Proc. Soc. Exp. Biol. Med.*, 219:109–119, 1998.
Mlsna et al., *Protein Sci.*, 2:429–435, 1993.
Munishkin and Wool, *J. Biol. Chem.*, 270:30581–30587, 1995.
Nakamura et al., In: *Enzyme Immunoassays: Heterogeneous and Homogeneous Systems*, Chapter 27, 1987.
Nowlin et al., *J. Biol. Chem.*, 268:20352–20359, 1993.
O'Hare et al., *Febs Lett.*, 216(1):73–78, 1987.
Orucevic and Lala, *J. Immunother.*, 18:210–220, 1995.
O'Shannessy et al., *J. Immun. Meth.*, 99, 153–161, 1987.
Owens & Haley, *J. Biol. Chem.*, 259:14843–14848, 1987.

PCT Patent Application WO 91/16347
Potter & Haley, *Meth. in Enzymol.*, 91, 613–633, 1983.
Press et al., *J. Immun.* 141:4410, 1988.
Puri and Rosenberg, *Cancer Immunol. Immunother.*, 28:267–274, 1989.
Puri et al., *Cancer Res.*, 49:969–976, 1989.
Rabinovich et al., "Vaccine technologies: view to the future," *Science*, 265(5177):1401–1404, 1994.
Remington's Pharmaceutical Sciences, 16th Ed. Mack Publishing Company, 1980.
Rosenberg et al., *N. Engl. J. Med.*, 316:889–897, 1987.
Rosenstein et al., *J. Immunol.*, 137:1735–1742, 1986.
Rosenthal, 1937.
Sambrook et al., *In: Molecular Cloning: A Laboratory Manual*, Vol. 1, Cold Spring Harbor Laboratory Press, Cold Spring Harbor, N.Y., Ch. 7,7.19–17.29, 1989.
Sasso et al., *J. Immunol.*, 142:2778–2783, 1989.
Sausville and Vitetta, *In: Monoclonal Antibody-Based Therapy of Cancer*, Grossbard (ed.), 4:81–89, 1997.
Shorki et al., *J. Immunol.*, 146:936–940, 1991.
Silvermann et al., *J. Clin. Invest.*, 96:417–426, 1995.
Simpson et al., *Eur. J. Biochem.*, 232:458–463, 1995.
Snapper et al., "Lysogeny and transformation in mycobacteria: stable expression of foreign genes," *Proc Natl Acad Sci USA.* 85(18):6987–6991, 1988.
Soler-Rodriguez et al., "Ricin A-chain and ricin A-chain immunotoxins rapidly damage human endothelial cells: implications for vascular leak syndrome," *Exp. Cell Res.*, 206:227–234, 1993.
Soler-Rodriguez et al., *Exp. Cell Res.*, 206:227–234, 1993.
Soler-Rodriguez et al., *Int. J. Immunopharm.*, 14(2):281–291, 1992.
Takada et al., "Molecular and structural requirements of a lipoteichoic acid from *Enterococcus hirae* ATCC 9790 for cytokine-inducing, antitumor, and antigenic activities," *Infect Immun.* 63(1):57–65, 1995.
Tselepis et al., *J. Biol. Chem.*, 272:21341–21348, 1997.
U.S. Pat. No. 3,791,932
U.S. Pat. No. 3,817,837
U.S. Pat. No. 3,850,752
U.S. Pat. No. 3,939,350
U.S. Pat. No. 3,949,064
U.S. Pat. No. 3,996,345
U.S. Pat. No. 4,174,384
U.S. Pat. No. 4,275,149
U.S. Pat. No. 4,277,437
U.S. Pat. No. 4,366,241
U.S. Pat. No. 4,435,386
U.S. Pat. No. 4,436,727
U.S. Pat. No. 4,436,728
U.S. Pat. No. 4,472,509
U.S. Pat. No. 4,505,899
U.S. Pat. No. 4,505,900
U.S. Pat. No. 4,520,019
U.S. Pat. No. 4,578,770
U.S. Pat. No. 4,579,945
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,664,911
U.S. Pat. No. 4,682,195
U.S. Pat. No. 4,683,202
U.S. Pat. No. 4,792,447
U.S. Pat. No. 4,866,034
U.S. Pat. No. 4,877,611
U.S. Pat. No. 4,938,948
U.S. Pat. No. 4,950,645
U.S. Pat. No. 5,021,236
U.S. Pat. No. 5,045,451
U.S. Pat. No. 5,196,066
U.S. Pat. No. 5,578,706
U.S. Pat. No. 5,686,072
Vial and Descotes, *Drug Safety*, 7:417–433, 1992.
Vitetta et al., *Immunol. Today*, 14:252–259, 1993.
Wayner and Kovach, *J. Cell Biol.*, 116:489–497, 1992.
Yamamoto et al., 1988.
Yeh et al., *Blood*, 292:3268–3276, 1998.
Yin et al., 1989.

What is claimed is:

1. A modified proteinaceous composition comprising a ricin A chain having a Leu-Asp-Val subsequence that has been altered, wherein induction of vascular leak syndrome by the modified proteinaceous composition is reduced as compared to native ricin A chain toxin.

2. The modified proteinaceous composition of claim 1, wherein said Leu-Asp-Val sequence is on a surface of the native ricin A chain toxin.

3. The modified proteinaceous composition of claim 1, wherein at least one of Leu, Asp, or Val of the native Leu-Asp-Val amino acid sequence has been altered to another amino acid.

4. The modified proteinaceous composition of claim 3, wherein at least one of Leu, Asp, or Val of the native Leu-Asp-Val amino acid sequence has been deleted.

5. The modified proteinaceous composition of claim 1, further defined as comprising at least one additional amino acid sequence alteration, relative to a native ricin A chain amino acid sequence, wherein the at least one additional amino acid sequence alteration is to a sequence flanking the Leu-Asp-Val sequence.

6. The modified proteinaceous composition of claim 5, wherein the at least one additional amino acid sequence alteration comprises a mutation to the native amino acid sequence.

7. The modified proteinaceous composition of claim 5, wherein the at least one additional amino acid sequence alteration comprises a deletion from the native amino acid sequence.

8. The modified proteinaceous composition of claim 5, wherein the at least one additional amino acid sequence alteration is C-terminal to the Leu-Asp-Val sequence.

9. The modified proteinaceous composition of claim 5, wherein the at least one additional amino acid sequence alteration is N-terminal to the Leu-Asp-Val sequence.

10. A modified ricin A chain toxin comprising at least one alteration to the Leu-Asp-Val sequence at amino acid residues 74–76 of native ricin A chain as set forth in SEQ ID NO:1, wherein induction of vascular leak syndrome by the modified toxin is reduced as compared to the native ricin A chain.

11. The modified ricin A chain toxin of claim 10, wherein the leucine at amino acid residue 74 of native ricin A chain as set forth in SEQ ID NO:1 is altered.

12. The modified ricin A chain toxin of claim 10, wherein the aspartate at amino acid residue 75 of native ricin A chain as set forth in SEQ ID NO:1 is altered.

13. The modified ricin A chain toxin of claim 10, wherein the valine at amino acid residue 76 of native ricin A chain as set forth in SEQ ID NO:1 is altered.

14. The modified ricin A chain toxin of claim 10, further defined as comprising at least one additional amino acid sequence alteration, relative to a native amino acid sequence of the ricin A chain toxin, wherein the at least one additional amino acid sequence alteration is to a sequence flanking the Leu-Asp-Val sequence.

15. The modified ricin A chain toxin of claim 14, wherein the at least one additional amino acid sequence alteration comprises a mutation to the native amino acid sequence.

16. The modified ricin A chain toxin of claim 14, wherein the at least one additional amino acid sequence alteration comprises a deletion to the native amino acid sequence.

17. The modified ricin A chain toxin of claim 14, wherein the at least one additional amino acid sequence alteration is C-terminal to the Leu-Asp-Val sequence.

18. The modified ricin A chain toxin of claim 10, wherein the alteration to the Leu-Asp-Val sequence is a mutation to at least one of the amino acids of the Leu-Asp-Val sequence, wherein one or more of the amino acids of said Leu-Asp-Val sequence is changed to a different amino acid.

19. The modified ricin A chain toxin of claim 10, wherein the at least one alteration to the Leu-Asp-Val sequence is a deletion of at least one of the amino acids in the Leu-Asp-Val sequence.

* * * * *